United States Patent
Sakano et al.

(10) Patent No.: US 9,423,355 B2
(45) Date of Patent: Aug. 23, 2016

(54) PLURAL CAMERA IMAGES CAPTURING AND PROCESSING APPARATUS, AND COMPOSITE IMAGING METHOD

(71) Applicant: HITACHI, LTD., Tokyo (JP)

(72) Inventors: Shinji Sakano, Tokyo (JP); Yuichi Nonaka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 401 days.

(21) Appl. No.: 14/173,840

(22) Filed: Feb. 6, 2014

(65) Prior Publication Data

US 2014/0240451 A1 Aug. 28, 2014

(30) Foreign Application Priority Data

Feb. 22, 2013 (JP) ................................. 2013-032713

(51) Int. Cl.
| | |
|---|---|
| *G01N 21/88* | (2006.01) |
| *H04N 5/232* | (2006.01) |
| *G06T 3/40* | (2006.01) |
| *H04N 5/247* | (2006.01) |

(52) U.S. Cl.
CPC .......... *G01N 21/8806* (2013.01); *G06T 3/4038* (2013.01); *H04N 5/23238* (2013.01); *H04N 5/247* (2013.01)

(58) Field of Classification Search
CPC .. G01N 21/8806; G06T 3/4038; H04N 5/247; H04N 5/23238
See application file for complete search history.

(56) References Cited

U.S. PATENT DOCUMENTS

| | | | | |
|---|---|---|---|---|
| 2003/0026469 A1* | 2/2003 | Kreang-Arekul | ........ | G06K 9/32 382/132 |
| 2009/0231630 A1* | 9/2009 | Sakai | .................. | B41J 11/0065 358/3.28 |
| 2009/0296207 A1* | 12/2009 | Goelles | ................ | G02B 21/008 359/385 |
| 2011/0188726 A1* | 8/2011 | Nathaniel | .............. | G01N 23/04 382/132 |

FOREIGN PATENT DOCUMENTS

JP 09-161068 A 6/1997

* cited by examiner

*Primary Examiner* — Kate Luo
(74) *Attorney, Agent, or Firm* — Mattingly & Malur, PC

(57) ABSTRACT

A plural camera images capturing and processing apparatus includes a plurality of cameras that capture images of a plurality of adjacent imaging regions which overlap each other, a plurality of laser devices that give a marker to each common imaging region in which imaging regions overlap each other, an imaging control unit that controls each camera and each laser device and acquires a markerless image group to which no marker is given and a marker-given image group to which the marker is given, a non-visible light image processing unit that calculates a correction parameter, which is information for aligning the inclinations, sizes, and positions of the imaging regions, on the basis of the marker-given image group, and a visible light image processing unit that composes the markerless image group to generate a composite image, on the basis of the correction parameter.

14 Claims, 23 Drawing Sheets

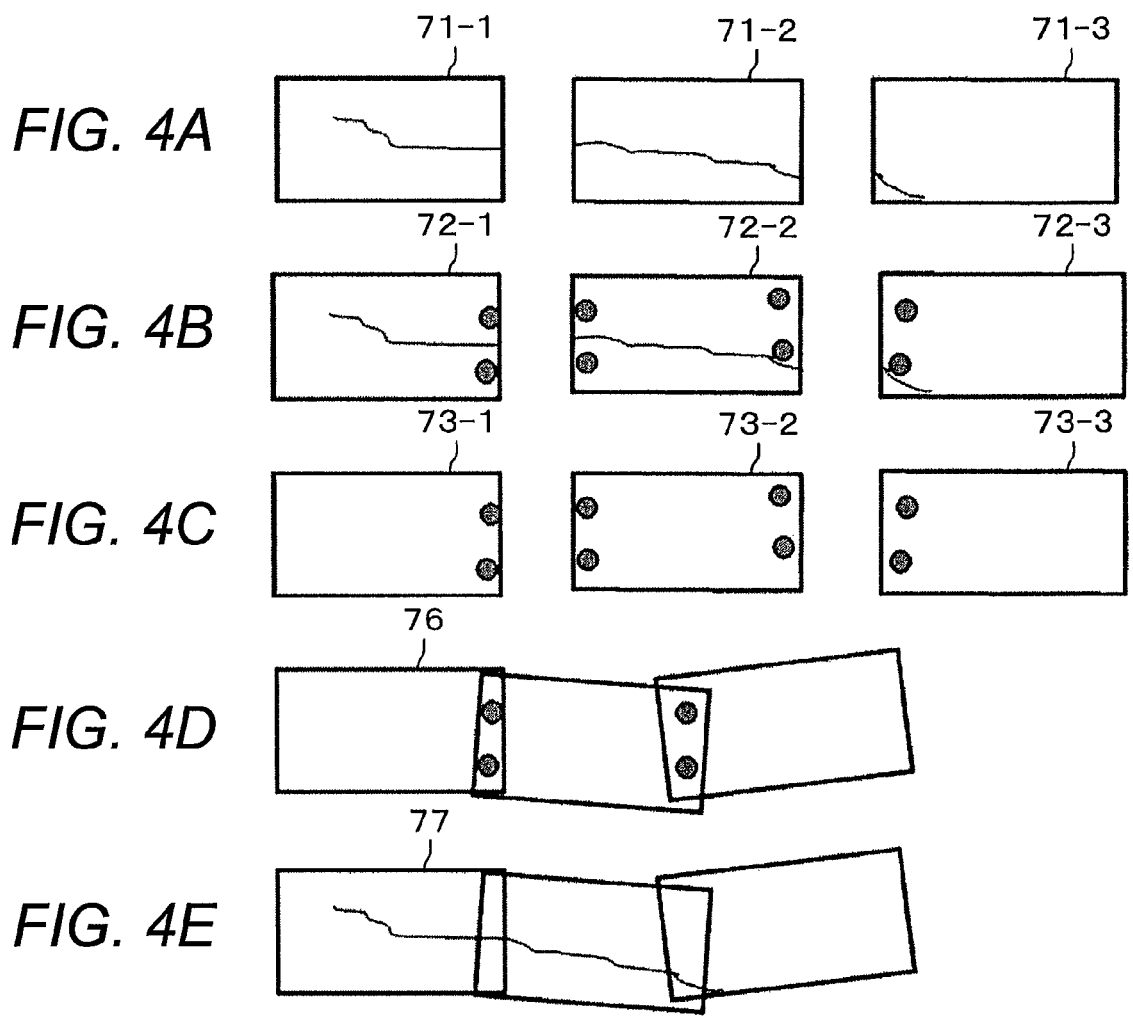

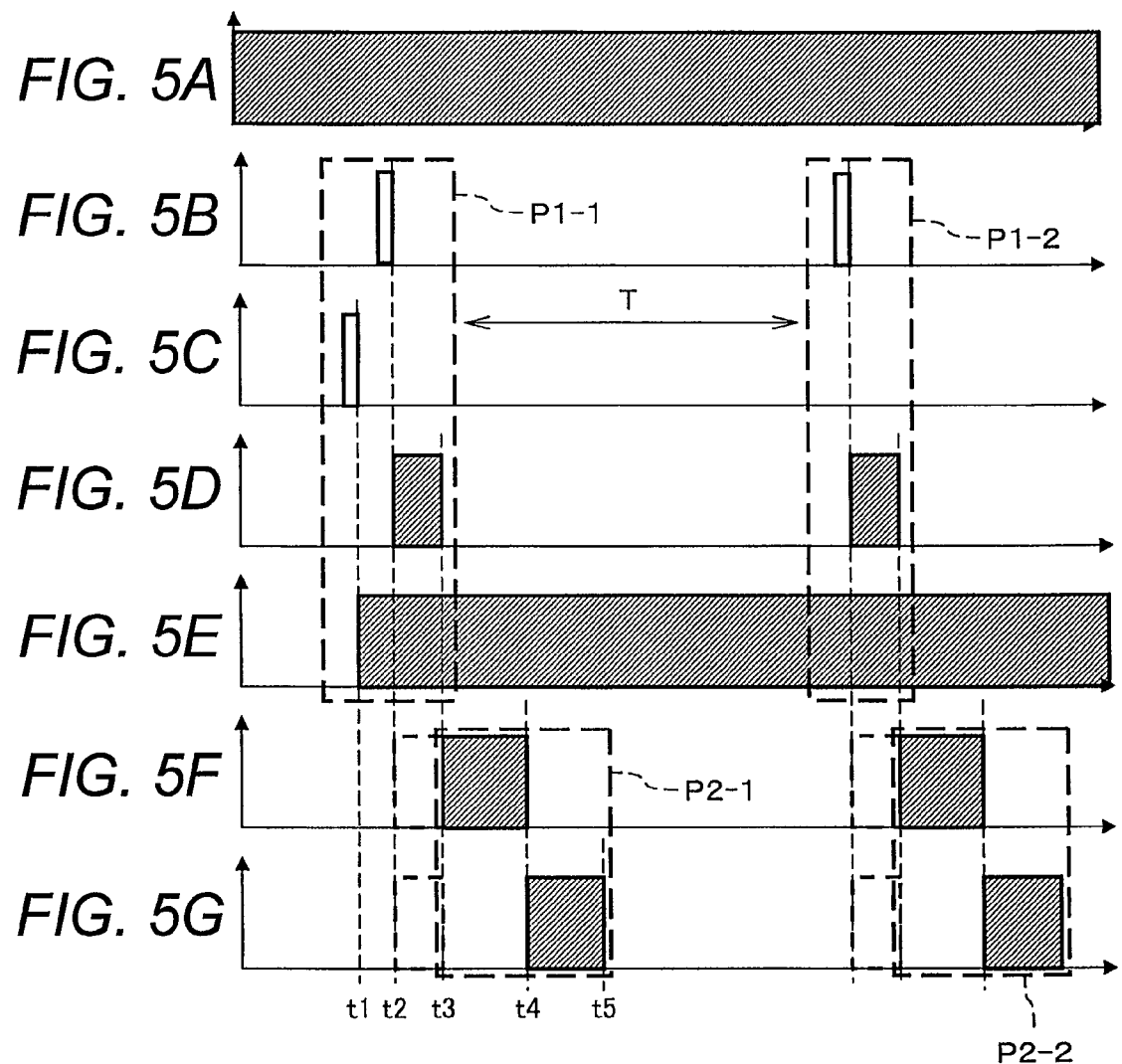

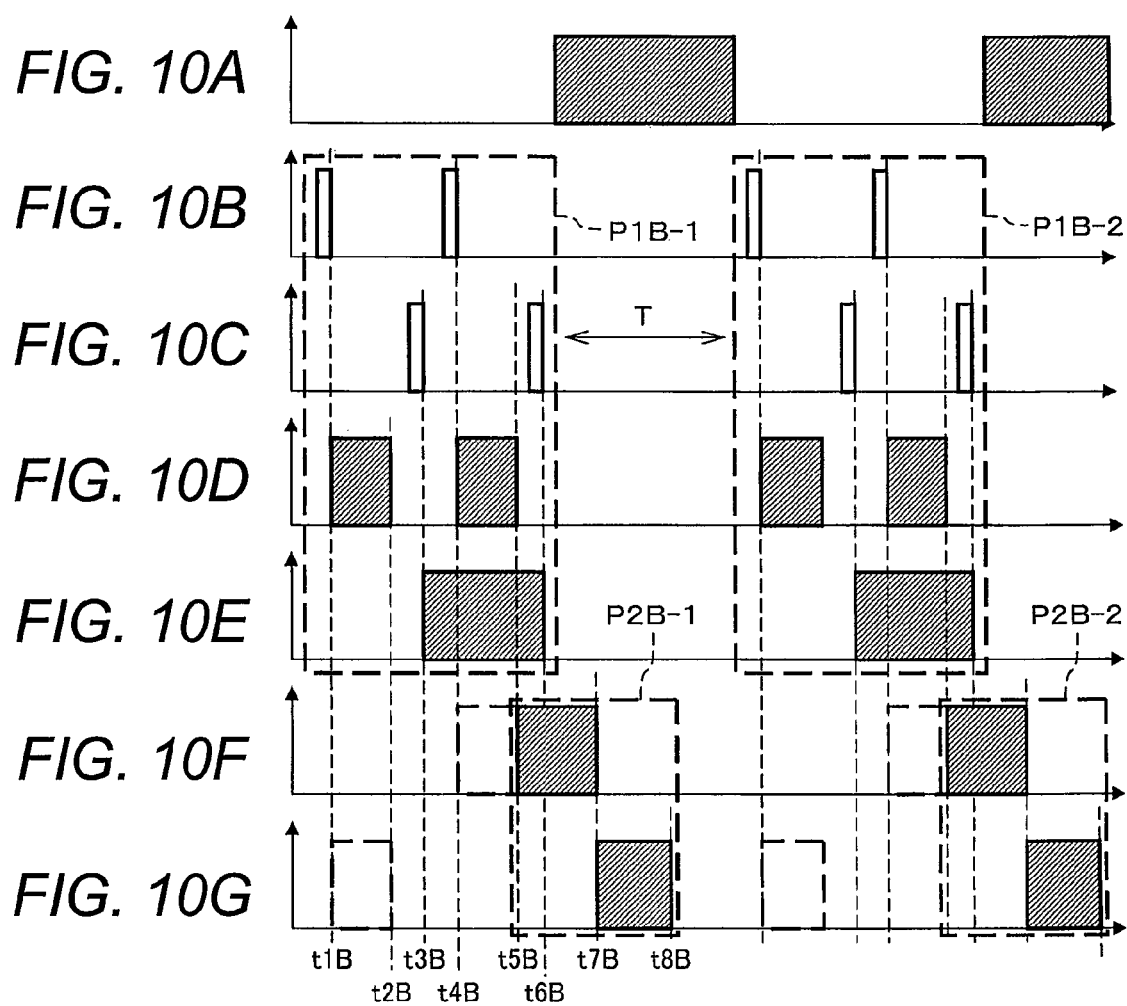

FIG. 12A 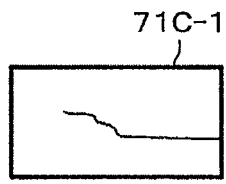 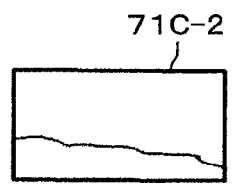 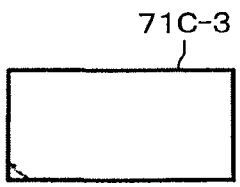
FIG. 12B 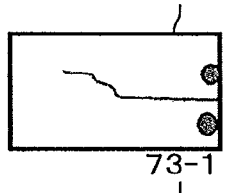 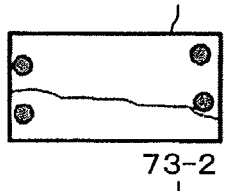 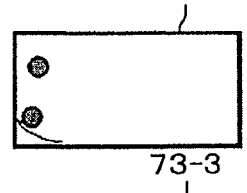
FIG. 12C 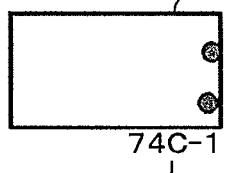 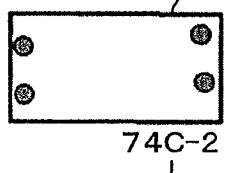 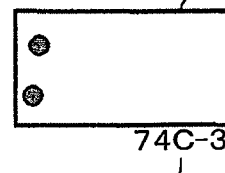
FIG. 12D 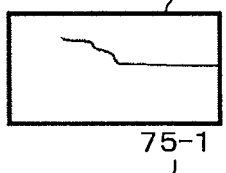 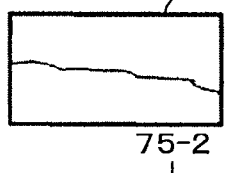 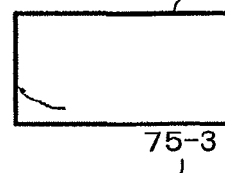
FIG. 12E 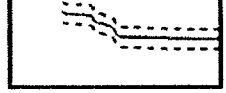 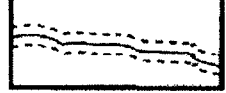 

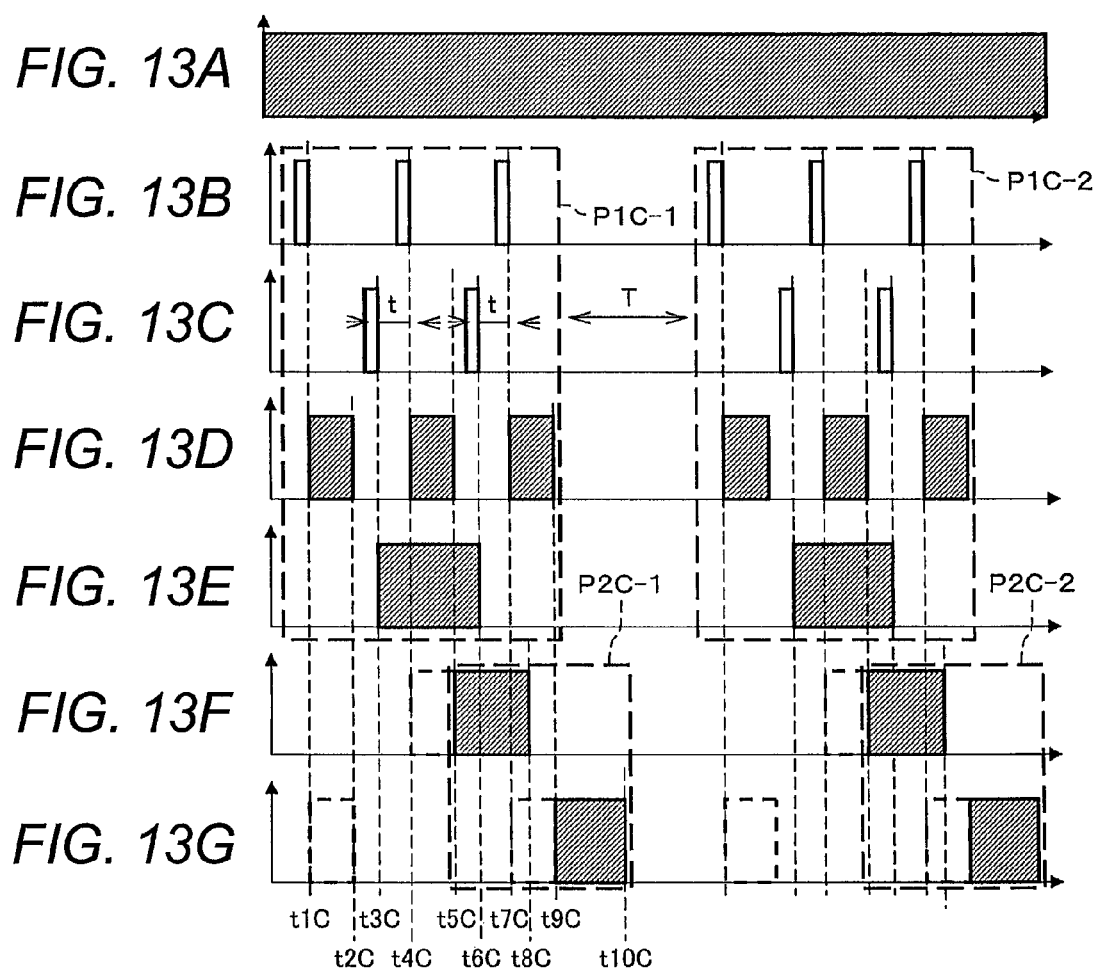

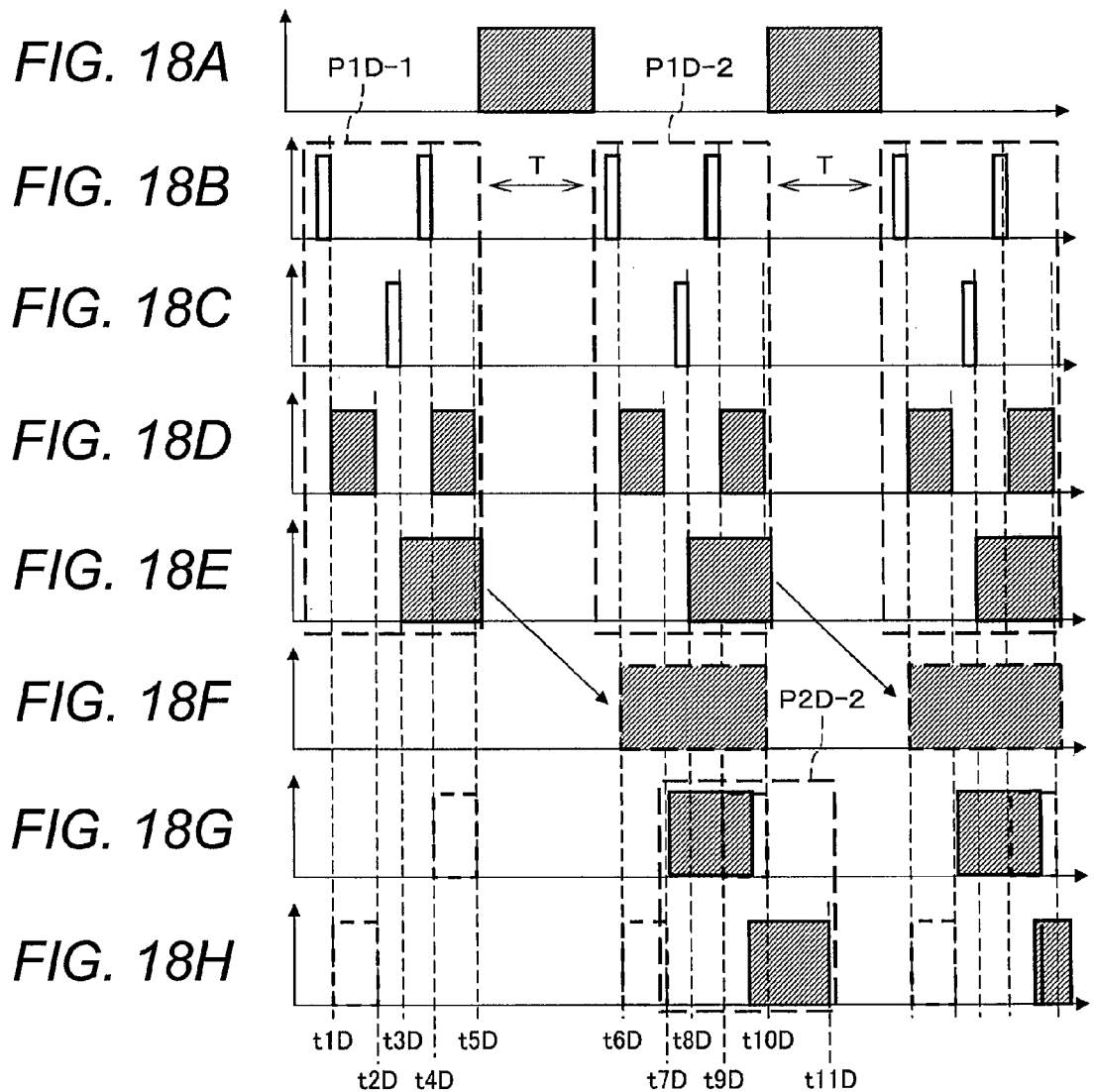

PLURAL CAMERA IMAGES CAPTURING AND PROCESSING APPARATUS, AND COMPOSITE IMAGING METHOD

CROSS-REFERENCE TO RELATED APPLICATION

This application claims the priority of Japanese Patent Application No. 2013-032713 filed Feb. 22, 2013, which is incorporated herein by reference in its entirety.

BACKGROUND OF THE INVENTION

1. Field of the Invention

The present invention relates to a plural camera images capturing and processing apparatus and a composite imaging method which capture an image of a wide area with high resolution.

2. Description of the Related Art

In recent years, structures, such as bridges or tunnels which have been constructed during the high-growth period, have started to reach their expected lifetime. Therefore, there is an increasing demand for inspecting the damaged state of the structures and determining the necessity for restoring or repairing the structures. In the technique according to the related art which inspects the damaged state of the structures, when it is difficult for an inspector to inspect the structure on the road, the inspector observes the structure with the naked eye using the scaffold. However, in recent years, an observation technique using a camera has been introduced in order to reduce costs for the scaffold and to ensure the safety of the inspector.

In the inspection of the damaged state of the structure, the area of an inspection range is large and cracks to be inspected are fine. Therefore, there is a concern that resolution will be insufficient in a single captured image. In the observation technique using the camera, in many cases, the images captured by a plurality of cameras (multiple cameras) are composed to generate a high-resolution image.

As a method of composing the images captured by a plurality of cameras into a high-resolution image, there is a method which searches for a common object from adjacent captured images and connects the images on the basis of the common object.

For example, JP-9-161068-A discloses a method which composes the images captured by a plurality of cameras into one high-resolution image. In JP-9-161068-A, paragraph 0011 discloses that "a laser beam is radiated to an object 2 in the imaging field of view of a CCD camera 1 and the image of the object 2 is captured by the same CCD camera 1". Paragraph 0012 discloses that "a laser beam is radiated to an object 2 including at least a common imaging portion in the imaging field of view of each of two or more CCD cameras 1 and the image of the object 2 is captured by the CCD cameras 1". Paragraph 0018 discloses that "laser beams emitted from a laser device 3 are a plurality of spot beams". Paragraph 0019 discloses that "laser beams emitted from a laser device 3 are two or more line beams which intersect each other". In JP-9-161068-A, paragraph 0049 discloses that "the field of view of the camera 1 or the laser beam irradiation direction of the laser device 3 is preferably set with allowance, considering the positional deviation of the carriage 10".

The method which searches for the common object from adjacent captured images and composes the images on the basis of the common object has the problem that a high-speed processing device or a lot of processing time is required. In addition, in some cases, the common object is not detected from adjacent captured images. For example, the common object is not detected when there is no characteristic object in the common imaging region (for example, the surface of a white wall) and when the image of an object with a repetitive pattern is captured in the common imaging region and it is difficult to determine a common pattern. In this case, it is difficult to connect adjacent captured images.

According to the technique disclosed in JP-9-161068-A, a plurality of images are connected to each other, using the laser beam (marker) as the common object. Therefore, it is possible to stably compose images, without taking a lot of processing time. However, the laser beam (marker) is included in the composite image and there is a concern that cracks to be inspected will be concealed by the laser beam.

SUMMARY OF THE INVENTION

An object of the invention is to provide a plural camera images capturing and processing apparatus and a composite imaging method which position a plurality of captured images using markers and generate a composite image without any marker problem.

In order to achieve the above object, according to an aspect of the invention, there is provided a plural camera images capturing and processing apparatus including: a plurality of imaging means that capture images of a plurality of adjacent imaging regions which overlap each other; one or a plurality of marker giving means that give a marker to each common imaging region in which the imaging regions overlap each other; an imaging control means that controls the imaging means and the marker giving means and acquires a markerless image group in which no marker is given to the common imaging region and a marker-given image group in which the marker is given to the common imaging region; a correction parameter calculation means that calculates a correction parameter for connecting the imaging regions using the marker-given image group; and an image composition means that composes the markerless image group to generate a composite image on the basis of the correction parameter.

The correction parameter means information for aligning the inclinations, sizes, and positions of two imaging regions.

The other means will be described in the following embodiments of the invention.

According to the invention, it is possible to position a plurality of captured images using markers and generate a composite image without any marker problem.

BRIEF DESCRIPTION OF THE DRAWINGS

FIGS. 4A to 4E are diagrams illustrating a multi-camera imaging process according to the first embodiment;

FIGS. 5A to 5G are timing charts according to the first embodiment;

FIGS. 10A to 10G are timing charts according to the third embodiment;

FIGS. 12A to 12G are diagrams illustrating a multi-camera imaging process according to a fourth embodiment;

FIGS. 13A to 13G are timing charts according to the fourth embodiment;

FIGS. 18A to 18H are timing charts according to the fifth embodiment;

DESCRIPTION OF THE PREFERRED EMBODIMENTS

Hereinafter, embodiments of the invention will be described in detail with reference to the drawings. In each embodiment, a case in which cracks in the lower surface of a concrete bridge is observed will be described.

First Embodiment

A plural camera images capturing and processing apparatus according to a first embodiment includes an imaging means corresponding to visible light with a first wavelength and non-visible light with a second wavelength and a marker giving means which gives a marker of the non-visible light with the second wavelength.

Figure 1A:
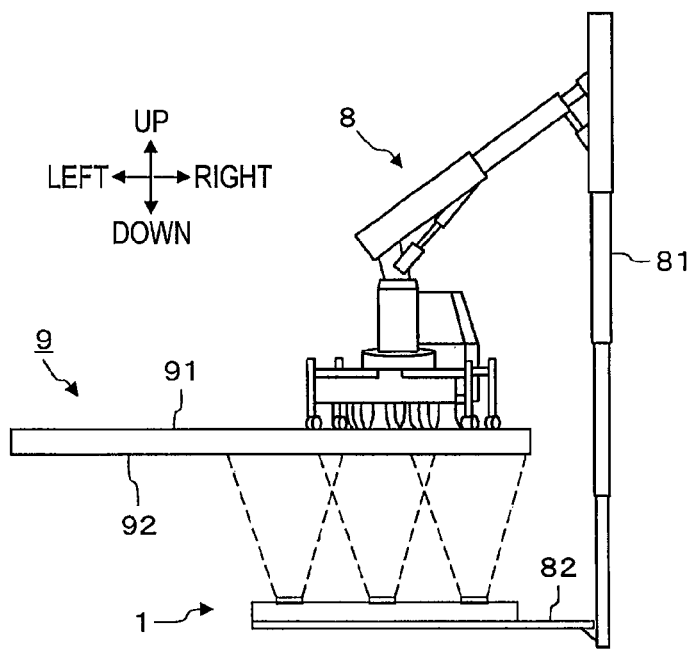
FIGS. 1A and 1B are diagrams illustrating the outward appearance and operation of a plural camera images capturing and processing apparatus according to a first embodiment.
Figure 1B:
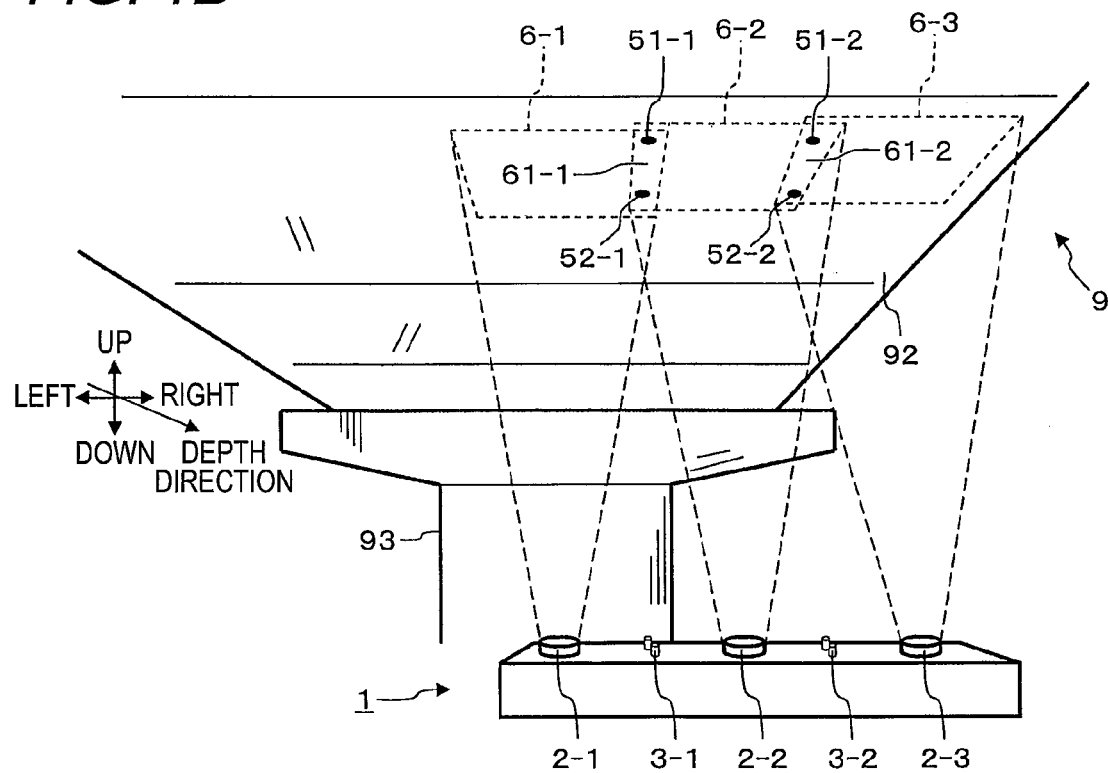

FIGS. 1A and 1B are diagrams illustrating the outward appearance and operation of a plural camera images capturing and processing apparatus 1 according to the first embodiment.

FIG. 1A is a diagram illustrating the outward appearance of a concrete bridge 9 which is an object to be captured, the plural camera images capturing and processing apparatus 1, and a bridge inspection vehicle 8 which supports the plural camera images capturing and processing apparatus 1.

A road 91 on which, for example, the bridge inspection vehicle 8 travels is on the concrete bridge 9. A lower surface 92 of the concrete bridge 9 is an object to be captured in this embodiment. An arm 81 is fixed to the bridge inspection vehicle 8 so as to be movable in all directions. A frame 82 is supported by the lower end of the arm 81. The plural camera images capturing and processing apparatus 1 is supported by the frame 82.

The plural camera images capturing and processing apparatus 1 captures the image of the lower surface 92 of the concrete bridge 9.

FIG. 1B is a diagram illustrating the operation of the plural camera images capturing and processing apparatus 1.

The concrete bridge 9 is supported by a pier 93. The plural camera images capturing and processing apparatus 1 is supported through the arm 81 and the frame 82 (which are not shown) below the lower surface 92 of the concrete bridge 9. The plural camera images capturing and processing apparatus 1 includes a plurality of cameras 2-1 to 2-3 (imaging means) and a plurality of laser devices 3-1 and 3-2 (marker giving means). Hereinafter, when the cameras 2-1 to 2-3 are not particularly distinguished from each other, they are simply referred to as cameras 2. When the laser devices 3-1 and 3-2 are not particularly distinguished from each other, they are simply referred to as laser devices 3.

The plurality of cameras 2-1 to 2-3, which are imaging means, are arranged on a straight line and are supported and fixed by the frame 82 (not shown) such that an imaging direction is an upward direction. The bridge inspection vehicle 8 shown in FIG. 1A is slowly moved, for example, in the depth direction to move the plural camera images capturing and processing apparatus 1 in the depth direction. Imaging regions 6-1 to 6-3 of the cameras 2-1 to 2-3 are arranged such that adjacent portions thereof overlap each other. Two infrared (non-visible light) laser beams 51-1 and 52-1, which are markers, are radiated to a common imaging region 61-1, which is an overlap region between adjacent imaging regions 6-1 and 6-2. Laser beams 51-2 and 52-2 are radiated to a common imaging region 61-2 which is an overlap region between adjacent imaging regions 6-2 and 6-3. Hereinafter, when the laser beams 51-1 and 51-2 are not particularly distinguished from each other, they are simply referred to as laser beams 51. When the laser beams 52-1 and 52-2 are not particularly distinguished from each other, they are simply referred to as laser beams 52.

The camera 2-1, which is an imaging means, captures the image of the imaging region 6-1. Similarly, the other cameras 2-2 and 2-3 capture the images of the imaging regions 6-2 and 6-3, respectively.

The laser device 3-1, which is a marker giving means, is arranged between adjacent cameras 2-1 and 2-2 and radiates two laser beams 51-1 and 52-1 to the common imaging region 61-1.

Similarly, the laser device 3-2 is arranged between adjacent cameras 2-2 and 2-3 and radiates two laser beams 51-2 and 52-2 to the common imaging region 61-2.

These laser beams 51 and 52 are not captured by a visible light imaging device, but can be captured by an infrared imaging device.

Figure 2:
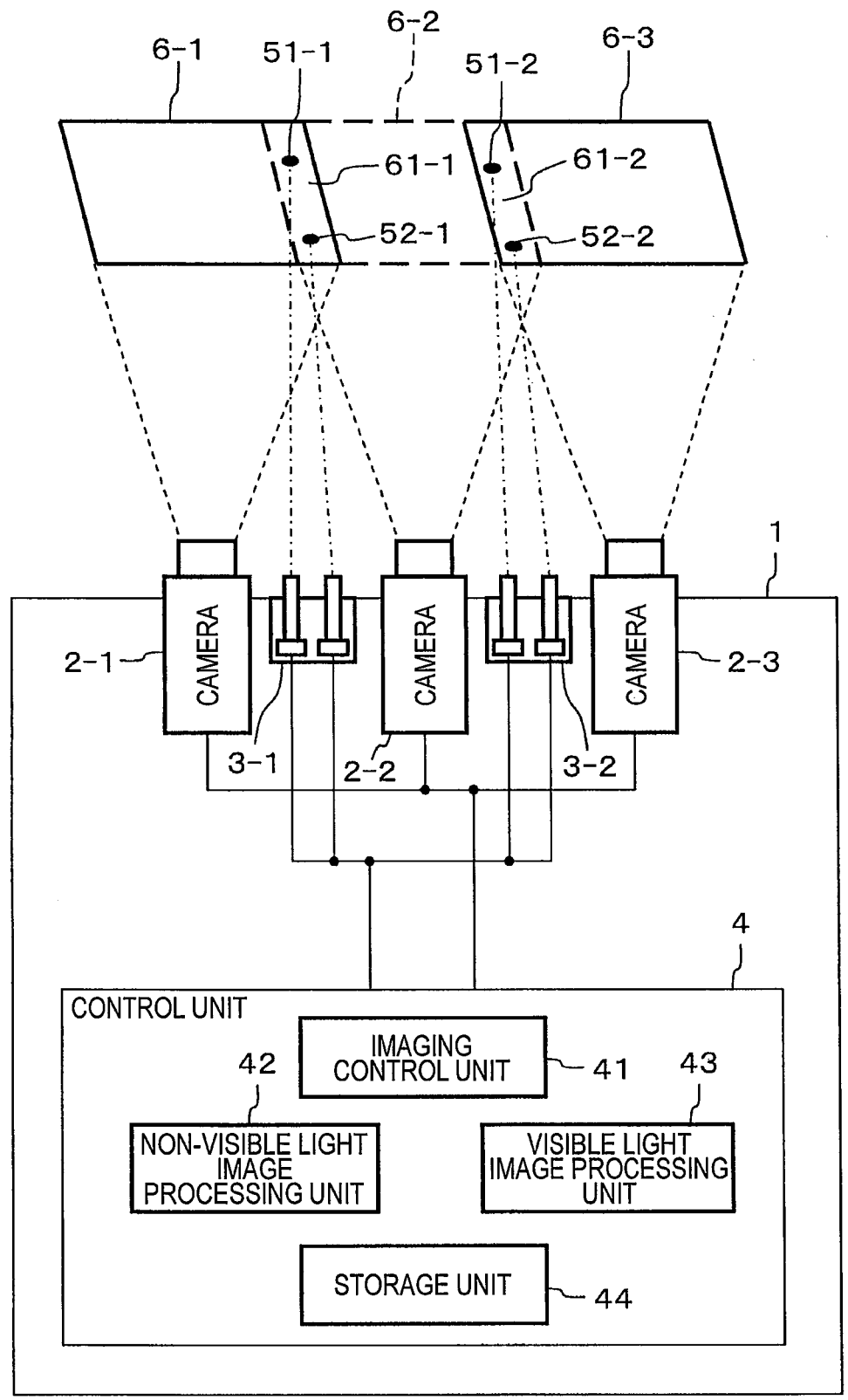
FIG. 2 is a diagram schematically illustrating the structure of the plural camera images capturing and processing apparatus according to the first embodiment.

FIG. 2 is a diagram schematically illustrating the structure of the plural camera images capturing and processing apparatus 1 according to the first embodiment.

The plural camera images capturing and processing apparatus 1 includes the cameras 2-1 to 2-3, the laser devices 3-1 and 3-2, and a control unit 4 which is connected to the cameras and the laser devices.

The cameras 2-1 to 2-3 are fixed at predetermined intervals on a straight line and capture the images of the imaging regions 6-1 to 6-3 in the same direction (upward direction). The cameras 2-1 to 2-3 can capture visible light images and non-visible light images of the imaging regions 6-1 to 6-3 at the same time. The structure of each of the cameras 2-1 to 2-3 will be described in detail with reference to FIGS. 3A and 3B, which will be described below.

The laser device 3-1 includes two laser oscillators and radiates two infrared laser beams 51-1 and 52-1, which are markers, to the common imaging region 61-1 in which adjacent imaging regions 6-1 and 6-2 overlap each other. Similarly, the laser device 3-2 includes two laser oscillators and radiates two infrared laser beams 51-2 and 52-2, which are markers, to the common imaging region 61-2 in which adjacent imaging regions 6-2 and 6-3 overlap each other.

The control unit 4 includes an imaging control unit 41 (control means), a non-visible light image processing unit 42 (correction parameter calculation means), a visible light image processing unit 43 (image composition means), and a storage unit 44.

The imaging control unit 41 (control means) controls the cameras 2-1 to 2-3 and the laser devices 3-1 and 3-2 and acquires a visible light image group and a non-visible light image group. The visible light image group is a group of markerless images to which no marker is given. The non-visible light image group is a group of marker-given images, to each of which two markers are given by the infrared laser beams 51 and 52. Each image acquired by the imaging control unit 41 is stored in the storage unit 44.

The non-visible light image processing unit 42 (correction parameter calculation means) calculates a correction parameter, which is information for aligning the inclinations, sizes, and positions of the imaging regions 6, on the basis of each marker which is given to the non-visible light image group acquired by the imaging control unit 41.

The visible light image processing unit 43 (image composition means) composes the visible light image group to generate a composite image on the basis of the correction parameter.

The storage unit 44 is, for example, flash memory or a hard disk drive (HDD) and stores digital data which is typified by an image.

Figure 3A:
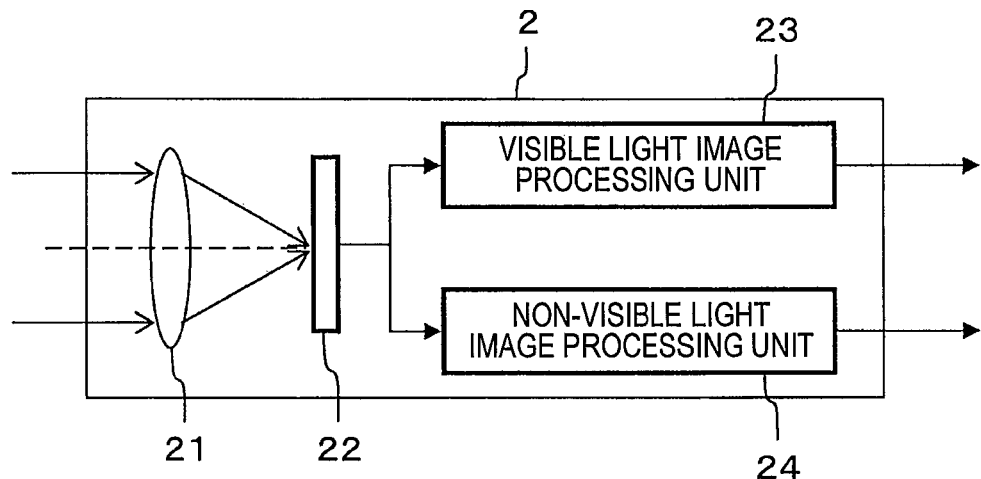
FIGS. 3A and 3B are diagrams illustrating the structure and operation of each camera according to the first embodiment.
Figure 3B:
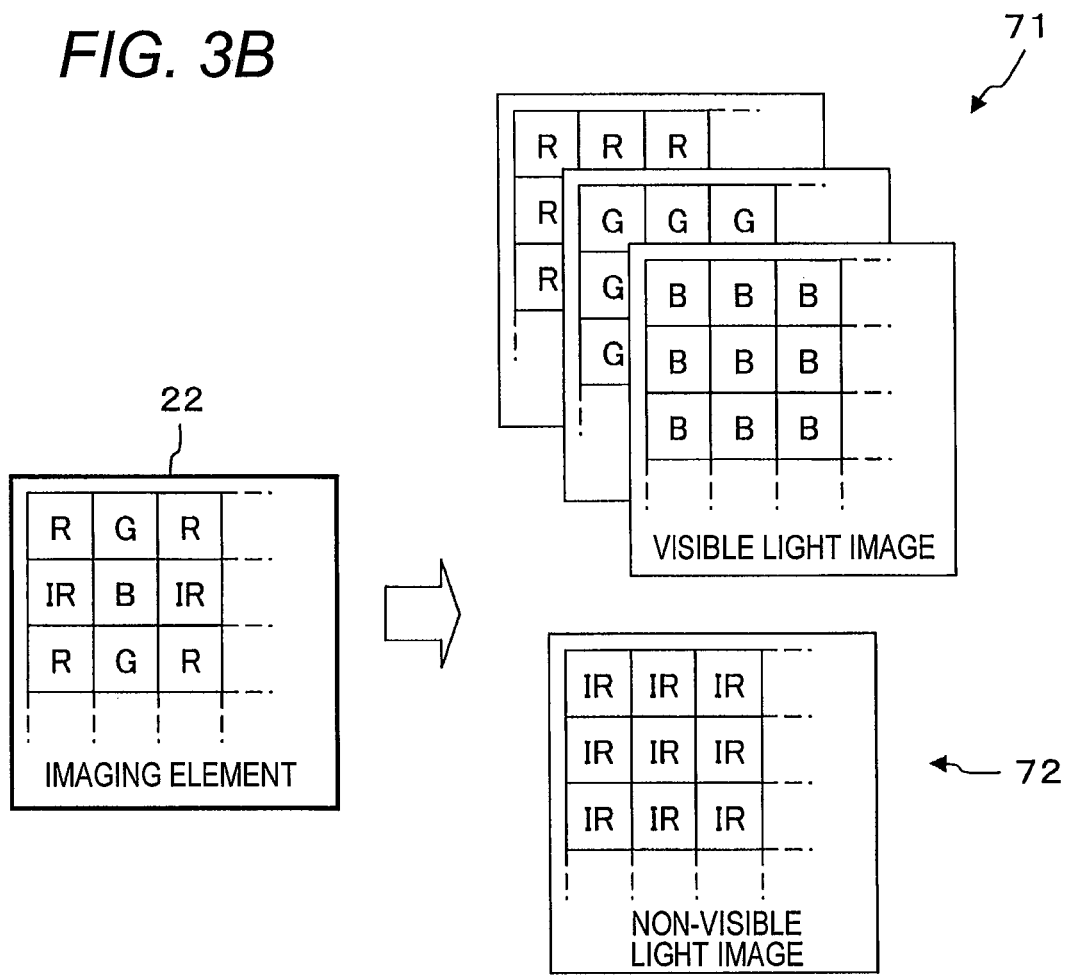

FIGS. 3A and 3B are diagrams illustrating the structure and operation of each camera 2 according to the first embodiment.

FIG. 3A is a diagram illustrating the structure of the camera 2.

The camera 2 includes a lens optical system 21 which focuses incident light to form an image, an imaging element 22 which converts the image into an electric signal, a visible light image processing unit 23 which generates a visible light image 71 from the electric signal converted by the imaging element 22, and a non-visible light image processing unit 24 which generates a non-visible light image 72 from the electric signal converted by the imaging element 22.

FIG. 3B is a diagram illustrating the structure and operation of the camera 2.

The imaging element 22 has a structure in which red (R), green (G), and blue (B) elements for visible light and an infrared (IR) element for non-visible light are arranged according to a predetermined rule. The visible light image 71 is generated on the basis of the electric signals of the R, G, and B elements for visible light which are output from the imaging element 22. The non-visible light image 72 is generated on the basis of the electric signal of the IR element for non-visible light which is output from the imaging element 22. In the camera 2 according to this embodiment, since an image is formed on a single imaging element 22 by the same lens optical system 21, it is possible to simultaneously capture the visible light image 71 and the non-visible light image 72 which have the same angle of view and are related to the same imaging region.

FIGS. 4A to 4E are diagrams illustrating a multi-camera imaging process according to the first embodiment.

FIG. 4A is a diagram illustrating a visible light image group.

Visible light images 71-1 to 71-3 in the visible light image group are output from the visible light image processing units 23 of the cameras 2-1 to 2-3, are acquired by the imaging control unit 41, and are stored in the storage unit 44.

FIG. 4B is a diagram illustrating a non-visible light image group.

Non-visible light images 72-1 to 72-3 in the non-visible light image group are output from the non-visible light image processing units 24 of the cameras 2-1 to 2-3, are acquired by the imaging control unit 41 and are stored in the storage unit 44.

FIG. 4C is a diagram illustrating a marker-extracted image group.

The non-visible light image processing unit 42 extracts marker portions of the non-visible light images 72-1 to 72-3 to generate marker-extracted images 73-1 to 73-3. Since the brightness of the marker portion is very high, a portion of the non-visible light image 72 in which brightness is equal to or greater than a predetermined value can be extracted as the marker portion.

FIG. 4D is a diagram illustrating a marker-corrected image 76.

The marker-corrected image 76 is obtained by adjusting the inclination and size of adjacent marker-extracted images 73-1 and 73-2 such that the positions of the markers are aligned with each other and by positioning the adjacent marker-extracted images 73-1 and 73-2. The non-visible light image processing unit 42 calculates a correction parameter for aligning the inclinations, sizes, and positions of the images and stores the parameter in the storage unit 44.

FIG. 4E is a diagram illustrating a markerless composite image.

A markerless composite image 77 is generated by adjusting the inclination and size of the visible light images 71-1 to 71-3 on the basis of the correction parameters and by positioning the visible light images 71-1 to 71-3. The markerless composite image 77 is the final product in the first embodiment.

FIGS. 5A to 5G are timing charts according to the first embodiment. In FIGS. 5A to 5G, the horizontal axis indicates time which is common to FIGS. 5A to 5G. Next, this embodiment will be described with reference to FIGS. 1 to 4.

FIG. 5A is a diagram illustrating the presence and absence of the movement of the plural camera images capturing and processing apparatus 1.

FIG. 5B is a diagram illustrating a camera imaging trigger.

FIG. 5C is a diagram illustrating a marker giving trigger.

FIG. 5D is a diagram illustrating an imaging time. The imaging time includes the processing time of the camera 2.

FIG. 5E is a diagram illustrating a marker giving time. In FIGS. 5B to 5E, a thick dashed line indicates an imaging period.

FIG. 5F is a diagram illustrating marker image processing. A thin dashed line indicates the processing time of the non-visible light image processing unit 24 in the camera 2. A solid line indicates the processing time of the non-visible light image processing unit 42 in the control unit 4.

FIG. 5G is a diagram illustrating markerless image processing. A thin dashed line indicates the processing time of the visible light image processing unit 23 in the camera 2. A solid line indicates the processing time of the visible light image processing unit 43 in the control unit 4. In FIGS. 5F and 5G, a thick dashed line indicates an image processing period.

The plural camera images capturing and processing apparatus 1 according to this embodiment is constantly moved in the depth direction by the bridge inspection vehicle 8 shown in FIGS. 1A and 1B.

At a time t1, the imaging control unit 41 generates the marker giving trigger. Then, an initial imaging period P1-1 starts. Then, the imaging control unit 41 operates each of the laser devices 3-1 and 3-2. The laser devices 3-1 and 3-2 radiate infrared laser beams 51 and 52.

At a time t2, the camera imaging trigger is generated. The imaging control unit 41 instructs the cameras 2-1 to 2-3 to capture a visible light image and a non-visible light image. The cameras 2-1 to 2-3 capture the visible light image group shown in FIG. 4A and the non-visible light image group shown in FIG. 4B to generate an image.

At a time t3, the imaging control unit 41 ends the acquisition of the visible light image group and the non-visible light image group from each camera 2. Then, the initial imaging period P1-1 ends and an initial image processing period P2-1 starts.

At a time t3, the non-visible light image processing unit 42 of the imaging control unit 41 processes the non-visible light image group to calculate the correction parameter.

At a time t4, the visible light image processing unit 43 of the imaging control unit 41 composes the visible light image group on the basis of the correction parameter.

At a time t5, the visible light image processing unit 43 of the imaging control unit 41 generates the markerless composite image 77 shown in FIG. 4E. Then, the initial image processing period P2-1 ends.

When a predetermined period of time has elapsed, the next imaging period P1-2 starts. When the next imaging period P1-2 ends, the next image processing period P2-2 starts. Similarly, the plural camera images capturing and processing apparatus 1 composes the visible light image group captured by the plurality of cameras 2-1 to 2-3 to generate the markerless composite image 77, which is a high-resolution image, and waits until the next imaging period.

When a time T has elapsed after the end of the initial imaging period P1-1, a second imaging period P1-2 starts and a second image processing period P2-2 starts with the start of the second imaging period P1-2.

Figure 6A:
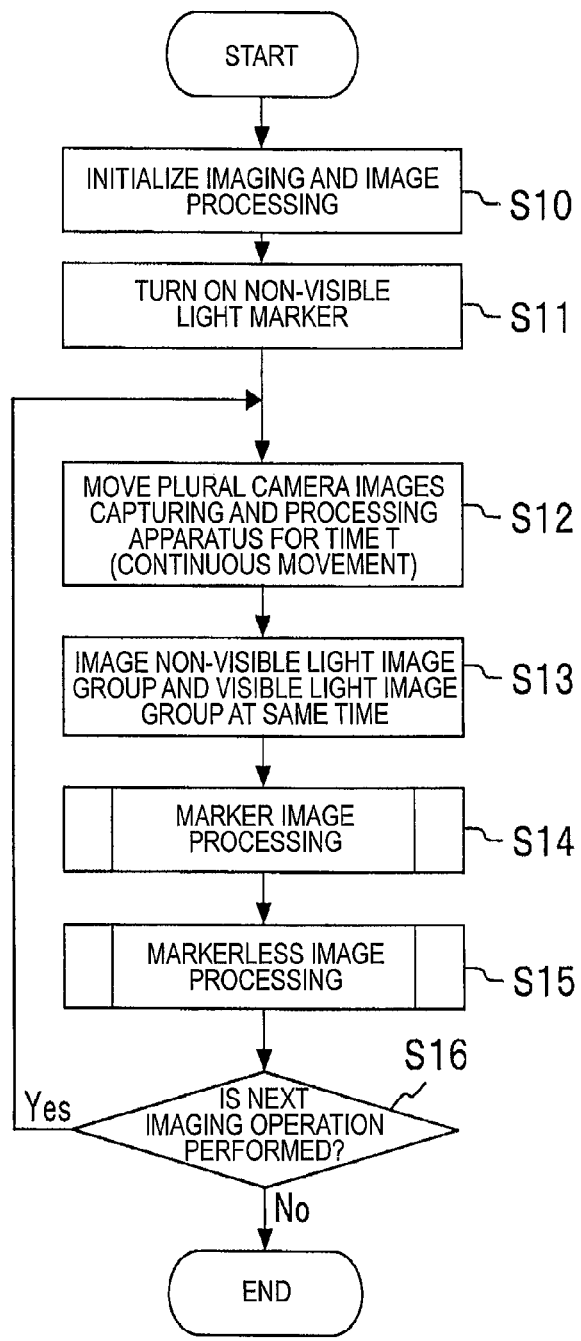
FIGS. 6A to 6C are flowcharts illustrating the multi-camera imaging process according to the first embodiment.
Figure 6B:
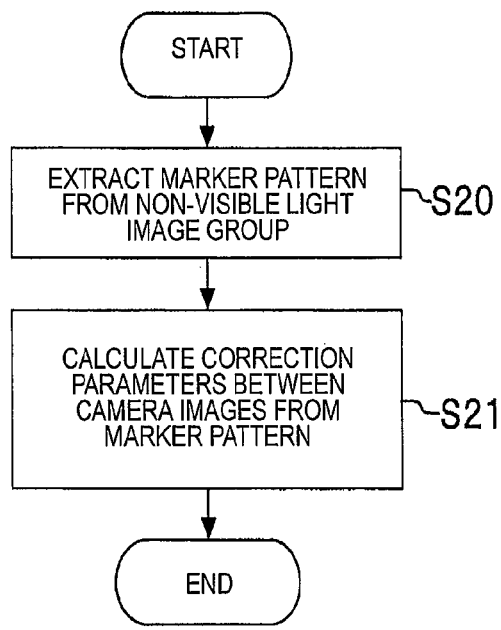
Figure 6C:
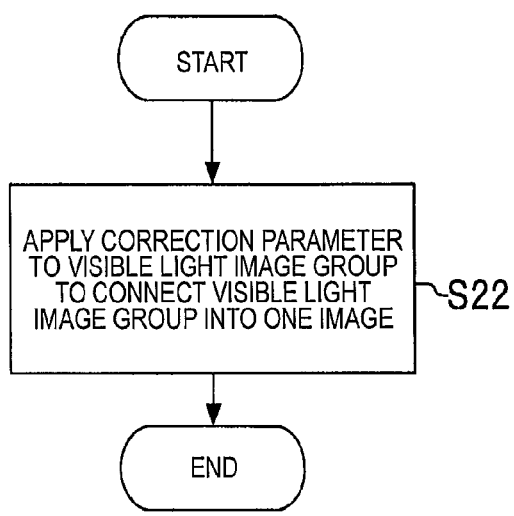

FIGS. 6A to 6C are flowcharts illustrating the multi-camera imaging process according to the first embodiment.

FIG. 6A is a flowchart illustrating the entire multi-camera imaging process.

When imaging starts, the plural camera images capturing and processing apparatus 1 starts the process shown in FIG. 6A.

In Step S10, the imaging control unit 41 initializes an imaging process and image processing.

In Step S11, the imaging control unit 41 turns on a non-visible light marker. The turn-on of the non-visible light marker means that the laser devices 3-1 to 3-2, which are marker giving means, are operated to radiate the infrared laser beams 51 and 52.

In Step S12, the plural camera images capturing and processing apparatus 1 is moved for the time T. Since the bridge inspection vehicle 8 supporting the plural camera images capturing and processing apparatus 1 keeps moving, the plural camera images capturing and processing apparatus 1 waits for the time T. In this way, the plural camera images capturing and processing apparatus 1 is moved for the time T. At first T is 0.

In Step S13, the imaging control unit 41 instructs the cameras 2-1 to 2-3 to simultaneously capture the non-visible light image group and the visible light image group using and acquires the captured non-visible light image group and visible light image group.

In Step S14, the imaging control unit 41 instructs the non-visible light image processing unit 42 to perform marker image processing. The marker image processing will be described in detail with reference to FIG. 6B, which will be described below.

In Step S15, the imaging control unit 41 instructs the visible light image processing unit 43 to perform markerless image processing. The markerless image processing will be described in detail with reference to FIG. 6C, which will be described below.

In Step S16, the imaging control unit 41 determines whether to perform the next imaging operation. When the determination conditions are satisfied (Yes), the imaging control unit 41 returns to Step S12. When the determination conditions are not satisfied (No), the imaging control unit 41 ends the process shown in FIG. 6A.

FIG. 6B is a flowchart illustrating in detail the marker image processing in Step S14.

The imaging control unit 41 calls the non-visible light image processing unit 42 and the marker image processing starts.

In Step S20, the non-visible light image processing unit 42 extracts a marker pattern from the non-visible light image group and generates a marker-extracted image group.

In Step S21, the non-visible light image processing unit 42 calculates the correction parameters between the camera images from the marker pattern and ends the marker image processing shown in FIG. 6B.

FIG. 6C is a flowchart illustrating in detail the markerless image processing in Step S15.

In Step S22, the visible light image processing unit 43 applies the correction parameter to the visible light image group to generate one markerless composite image 77 (see FIG. 4E). When the process in Step S22 ends, the visible light image processing unit 43 ends the markerless image processing shown in FIG. 6C.

Effects of First Embodiment

The above-described first embodiment has the following effects (A) and (B).

(A) The plural camera images capturing and processing apparatus 1 includes a plurality of laser devices 3 which emit the laser beams 51 and 52, which are non-visible light, and a plurality of cameras 2 which capture a non-visible light image and a visible light image related to the same imaging region 6 at the same time. Therefore, the non-visible light image groups are connected to each other on the basis of the laser beams 51 and 52, which are non-visible light, to calculate the correction parameter. As a result, for example, cracks to be inspected are not concealed by laser beams (markers).

(B) The camera 2 can capture the non-visible light image and the visible light image related to the same imaging region 6 at the same time. Therefore, the imaging region of a marker-given image is accurately aligned with the imaging region of a markerless image. As a result, it is possible to accurately connect and compose the markerless image group using the correction parameter calculated by the markers.

Second Embodiment

Figure 7A:
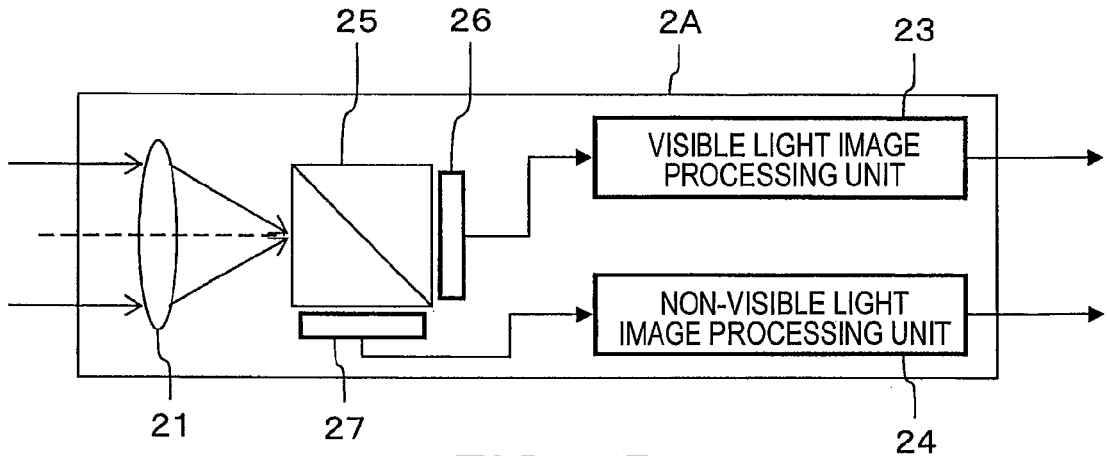
FIGS. 7A to 7C are diagrams illustrating the structure and operation of each camera according to a second embodiment.
Figure 7B:
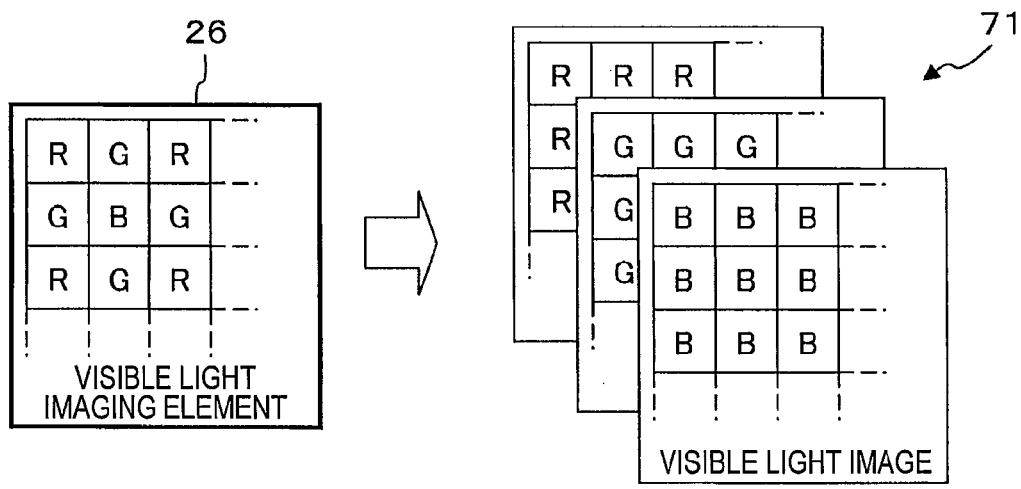

FIGS. 7A and 7B are diagrams illustrating the structure and operation of each camera 2A according to a second embodiment.

FIG. 7A is a diagram illustrating the structure of the camera 2A.

The camera 2A according to the second embodiment includes a dichroic prism 25, a visible light imaging element 26, and a non-visible light imaging element 27 in addition to the structure of the camera 2 according to the first embodiment.

The camera 2A a lens optical system 21 which focuses incident light to form an image, the dichroic prism 25 which separates the incident light into visible light and infrared rays, the visible light imaging element 26 which converts a visible light image into an electric signal, a visible light image processing unit 23 which generates a visible light image 71 from the electric signal converted by the visible light imaging element 26, the non-visible light imaging element 27 which converts an infrared image into an electric signal, and a non-visible light image processing unit 24 which generates a non-visible light image 72 from the electric signal converted by the non-visible light imaging element 27.

Figure 7C:
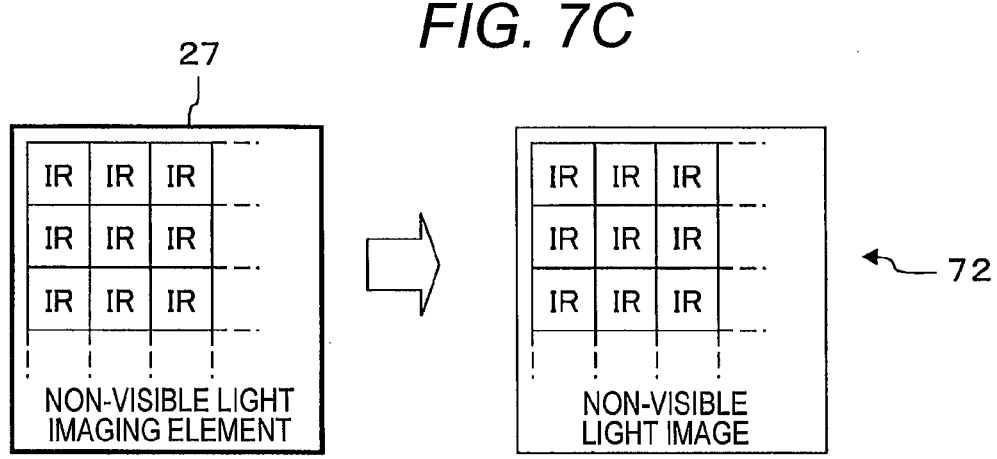

FIG. 7B is a diagram illustrating the structure and operation of the visible light imaging element 26. FIG. 7C is a diagram illustrating the structure and operation of the non-visible light imaging element 27.

The visible light imaging element 26 has a structure in which R, G, and B elements for visible light are arranged according to a predetermined rule. The non-visible light imaging element 27 has a structure in which an IR element for infrared light, which is non-visible light, is arranged according to a predetermined rule. The position of the visible light imaging element 26 and the non-visible light imaging element 27 is adjusted such that visible light imaging element 26 and the non-visible light imaging element 27 capture the image of the same imaging region 6.

The visible light image 71 is generated on the basis of the electric signals of the R, G, and B elements for visible light which are output from the visible light imaging element 26. The non-visible light image 72 is generated on the basis of the electric signal of the IR element for non-visible light which is output from the non-visible light imaging element 27. In the camera 2A according to this embodiment, images are formed on the visible light imaging element 26 and the non-visible light imaging element 27 by the same lens optical system 21. The position of the visible light imaging element 26 and the non-visible light imaging element 27 is adjusted such that the visible light imaging element 26 and the non-visible light imaging element 27 capture the image of the same imaging region 6. In this way, the camera 2A can capture the visible light image 71 and the non-visible light image 72 related to the same imaging region 6 at the same time.

Effects of Second Embodiment

The above-described second embodiment has the following effects (C) and (D).

(C) The camera 2A includes the visible light imaging element 26 and the non-visible light imaging element 27. Therefore, the camera 2A can capture a higher-resolution image than the camera 2 according to the first embodiment.

(D) In the camera 2A, the dichroic prism 25 separates incident light into visible light and infrared light. Therefore, durability and light permeability are more than those when an infrared transmission filter or an infrared removal filter is used to separate incident light into visible light and infrared light. The durability makes it possible to increase the lifespan of the camera 2A. In addition, high light permeability enables the camera 2A to capture images at a high shutter speed. Therefore, the camera 2A is suitable for imaging while the bridge inspection vehicle 8 is moving.

Third Embodiment

In this embodiment, an example of a plural camera images capturing and processing apparatus 1B for observing, for example, cracks in a lower surface 92 of a concrete bridge 9 will be described. In this embodiment, the plural camera images capturing and processing apparatus 1B is stopped during an imaging operation and is moved along the lower surface 92 after the imaging operation.

Figure 8:
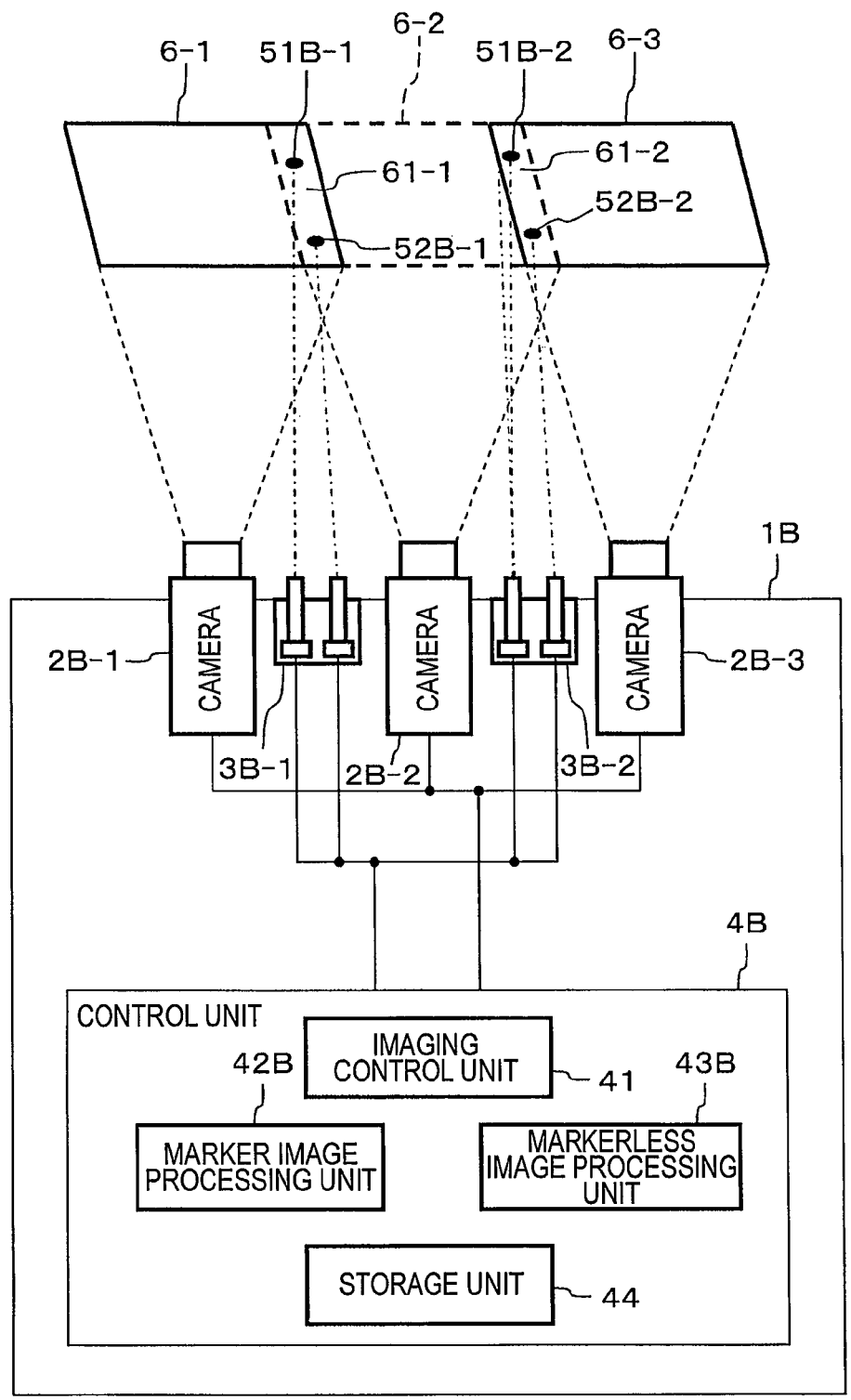
FIG. 8 is a diagram schematically illustrating the structure of a plural camera images capturing and processing apparatus according to a third embodiment.

FIG. 8 is a diagram schematically illustrating the structure of the plural camera images capturing and processing apparatus 1B according to the third embodiment.

The plural camera images capturing and processing apparatus 1B includes cameras 2B-1 to 2B-3 for visible light which are different from those in the first embodiment, laser devices 3B-1 and 3B-2 which are different from those in the first embodiment and radiate visible laser beams, and a control unit 4B which is connected to the cameras 2B-1 to 2B-3 and the laser devices 3B-1 and 3B-2. The laser device 3B-1 radiates visible laser beams 51B-1 and 52B-1 to a common imaging region 61-1. The laser device 3B-2 radiates visible laser beams 51B-2 and 52B-2 to a common imaging region 61-2. The other structures are the same as those of the plural camera images capturing and processing apparatus 1 according to the first embodiment.

Hereinafter, when the laser beams 51B-1 and 51B-2 are not particularly distinguished from each other, they are simply referred to as laser beams 51B. When the laser beams 52B-1 and 52B-2 are not particularly distinguished from each other, they are simply referred to as laser beams 52B.

The control unit 4B includes a marker image processing unit 42B (correction parameter calculation means) which is different from that in the first embodiment and a markerless image processing unit 43B (image composition means). The other structures are the same as those of the control unit 4 according to the first embodiment.

FIGS. 9A to 9E are diagrams illustrating a multi-camera imaging process according to the third embodiment.

Figure 9A:
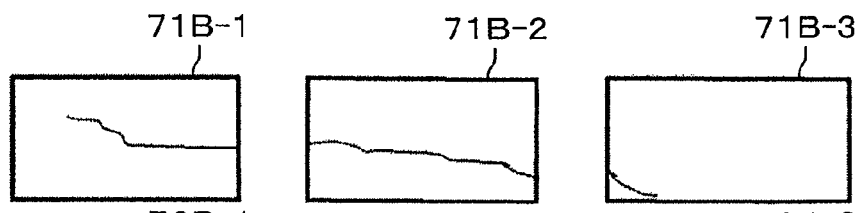
FIGS. 9A to 9E are diagrams illustrating a multi-camera imaging process according to the third embodiment.

FIG. 9A is a diagram illustrating a markerless image group.

Markerless images 71B-1 to 71B-3 are captured by the cameras 2B-1 to 2B-3, respectively, when the laser devices 3B-1 and 3B-2 are stopped. The imaging control unit 41 acquires the markerless images 71B-1 to 71B-3 from the cameras 2B-1 to 2B-3 and stores the markerless images 71B-1 to 71B-3 in the storage unit 44.

Figure 9B:
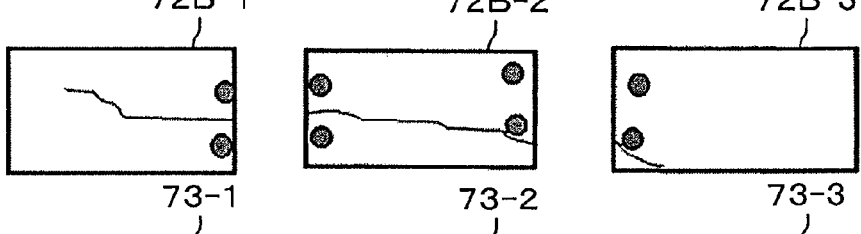

FIG. 9B is a diagram illustrating a marker-given image group.

Marker-given images 72B-1 to 72B-3 are captured by the cameras 2B-1 to 2B-3, respectively, when the laser devices 3B-1 and 3B-2 radiate the laser beams 51B and 52B. The imaging regions 6 related to the marker-given images 72B-1 to 72B-3 are the same as the imaging regions 6 related to the markerless images 71B-1 to 71B-3. The imaging control unit 41 acquires the marker-given images 72B-1 to 72B-3 from the cameras 2B-1 to 2B-3, respectively, and stores the marker-given images 72B-1 to 72B-3 in the storage unit 44.

Figure 9C:
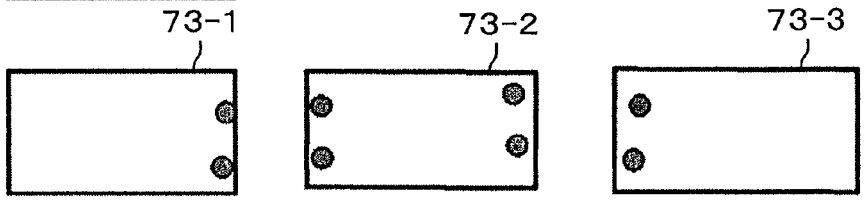

FIG. 9C is a diagram illustrating a marker-extracted image group.

In this embodiment, marker-extracted images 73-1 to 73-3 are the same as those in the first embodiment shown in FIG. 4C.

Figure 9D:
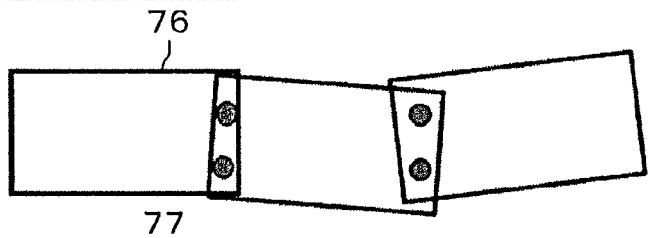

FIG. 9D is a diagram illustrating a marker-corrected image 76.

In this embodiment, the marker-corrected image 76 is the same as that in the first embodiment shown in FIG. 4D.

Figure 9E:
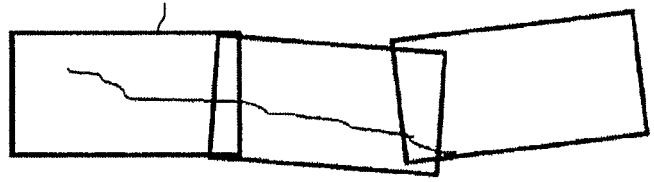

FIG. 9E is a diagram illustrating a markerless composite image 77.

In this embodiment, the markerless composite image 77 is the same as that in the first embodiment shown in FIG. 4E.

FIGS. 10A to 10G are timing charts according to third embodiment. In FIGS. 10A to 10G, the horizontal axis indicates time which is common to FIGS. 10A to 10G. Next, the timing charts will be described with reference to FIG. 8 and FIGS. 9A to 9E.

FIG. 10A is a diagram illustrating the presence or absence of the movement of the plural camera images capturing and processing apparatus 1B.

FIG. 10B is a diagram illustrating a camera imaging trigger.

FIG. 10C is a diagram illustrating a marker giving trigger.

FIG. 10D is a diagram illustrating an imaging time. The imaging time includes the processing time of the camera 2B.

FIG. 10E is a diagram illustrating a marker giving time. In FIGS. 10B to 10E, a thick dashed line indicates an imaging period.

FIG. 10F is a diagram illustrating marker image processing. A thin dashed line indicates the processing time of the camera 2. A solid line indicates the processing time of the marker image processing unit 42B of the control unit 4B.

FIG. 10G is a diagram illustrating markerless image processing. A thin dashed line indicates the processing time of the camera 2. A solid line indicates the processing time of the markerless image processing unit 43B in the control unit 4. In FIGS. 10F and 10G, a thick dashed line indicates an image processing period.

The plural camera images capturing and processing apparatus 1B according to this embodiment is stopped at a time t1B. When an imaging operation ends, the plural camera images capturing and processing apparatus 1B is moved in the depth direction until the next imaging operation starts.

At the time t1B, the imaging control unit 41 generates the camera imaging trigger. The cameras 2B-1 to 2B-3 capture the image of the lower surface 92. Then, an initial imaging period P1B-1 starts.

At a time t2B, the cameras 2B-1 to 2B-3 end image processing and output the markerless images 71B-1 to 71B-3, respectively. The imaging control unit 41 acquires the markerless images 71B-1 to 71B-3.

At a time t3B, the imaging control unit 41 generates the marker giving trigger and operates each laser device 3B. Each laser device 3B radiates the laser beams 51B and 52B, which are visible light, to the lower surface 92 of the concrete bridge 9.

At a time t4B, the imaging control unit 41 generates a camera imaging trigger. The cameras 2B-1 to 2B-3 capture the image of the lower surface 92 irradiated with the laser beams 51B and 52B.

At a time t5B, the cameras 2B-1 to 2B-3 end image processing and outputs the marker-given images 72B-1 to 72B-3. The imaging control unit 41 acquires the marker-given images 72B-1 to 72B-3 and starts marker image processing. Then, an initial image processing period P2B-1 starts.

At a time t6B, the imaging control unit 41 generates the marker giving trigger and stops each laser device 3B. In this way, the initial imaging period P1B-1 ends. Then, the plural camera images capturing and processing apparatus 1B is moved slowly in the depth direction until the next imaging operation starts.

At a time t7B, the marker image processing unit 42B ends the marker image processing, calculates a correction parameter, and processes the markerless image.

At a time t8B, the markerless image processing unit 43B ends the markerless image processing, generates the markerless composite image 77, and ends the initial image processing period P2B-1. When a time T has elapsed after the end of the initial imaging period P1B-1, a second imaging period P1B-2 starts and a second image processing period P2B-2 starts with the start of the second imaging period P1B-2.

Figure 11A:
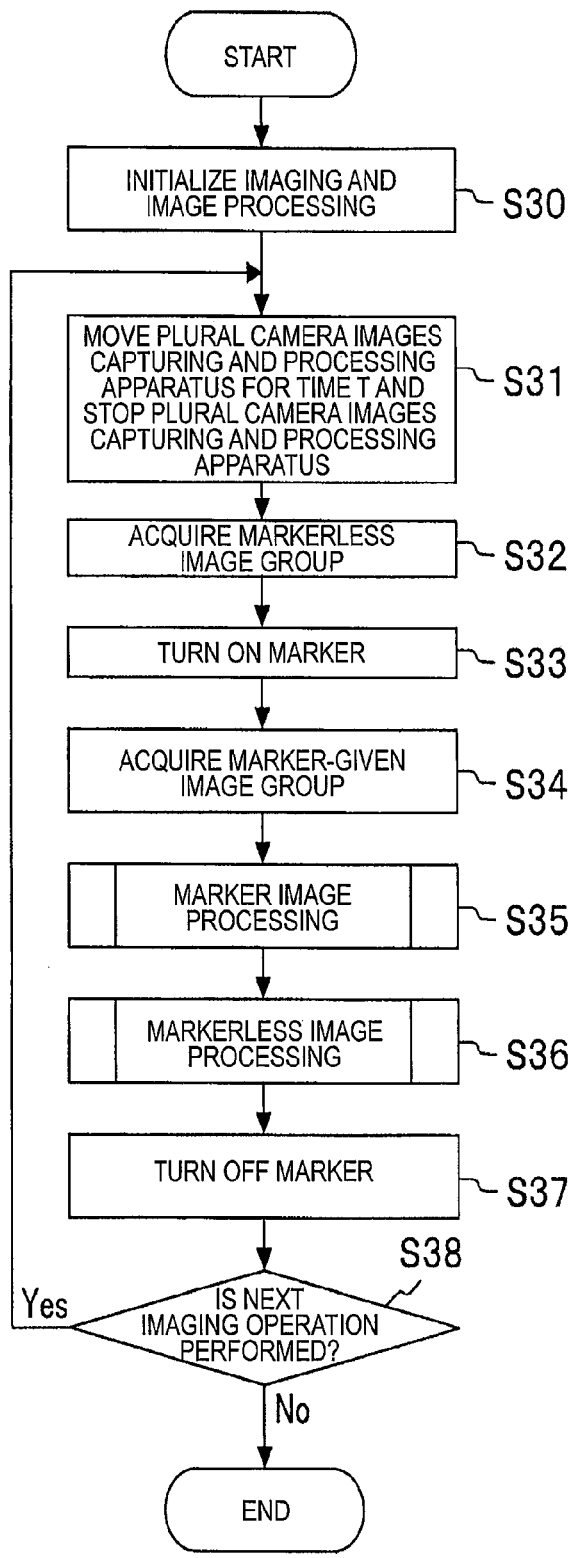
FIGS. 11A to 11C are flowcharts illustrating the multi-camera imaging process according to the third embodiment.
Figure 11B:
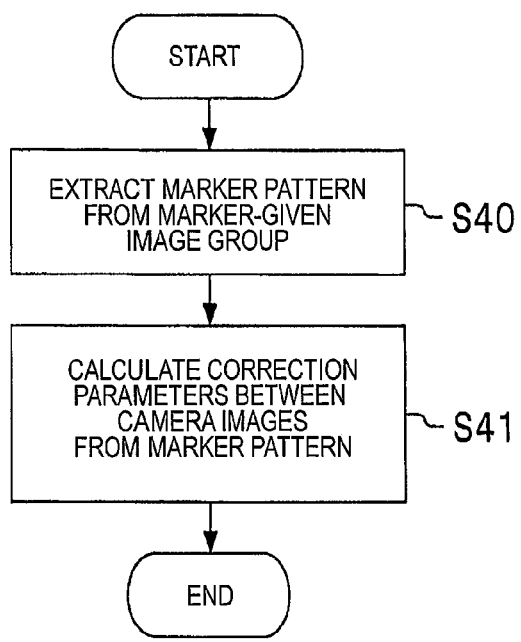
Figure 11C:
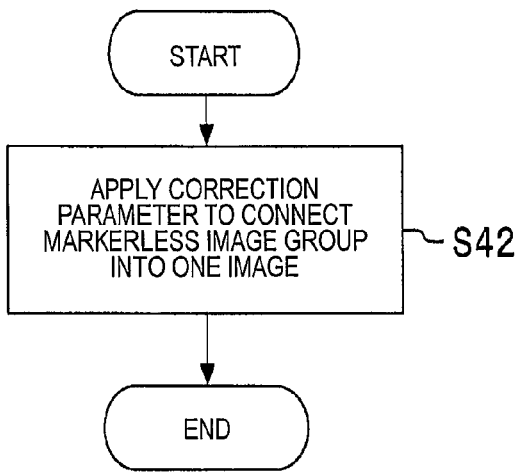

FIGS. 11A to 11C are flowcharts illustrating a multi-camera imaging process according to the third embodiment.

FIG. 11A is a flowchart illustrating the entire multi-camera imaging process.

When imaging starts, the plural camera images capturing and processing apparatus 1B starts the process shown in FIG. 11A.

In Step S30, the imaging control unit 41 initializes an imaging process and image processing.

In Step S31, the imaging control unit 41 waits until the plural camera images capturing and processing apparatus 1B is moved for the time T and is then stopped. The bridge inspection vehicle 8 supporting the plural camera images capturing and processing apparatus 1B intermittently repeats the moving operation for the time T and the imaging operation. At first T is 0.

In Step S32, the imaging control unit 41 instructs the cameras 2B-1 to 2B-3 to capture image groups and acquires the captured images. Since the laser devices 3B-1 and 3B-2 do not operate, the cameras 2B-1 to 2B-3 capture a markerless image group. The imaging control unit 41 acquires the markerless image group.

In Step S33, the imaging control unit 41 radiates the laser beams 51B and 52B to the imaging region 6 to turn on markers.

In Step S34, the imaging control unit 41 instructs the cameras 2B-1 to 2B-3 to capture image groups and acquires the captured images. Since the laser devices 3B-1 and 3B-2 operate, the cameras 2B-1 to 2B-3 capture marker-given image groups. The imaging control unit 41 acquires the marker-given image groups.

In Step S35, the imaging control unit 41 instructs the marker image processing unit 42B to perform marker image processing. The marker image processing will be described in detail with reference to FIG. 11B, which will be described below.

In Step S36, the imaging control unit 41 instructs the markerless image processing unit 43B to perform markerless image processing. The markerless image processing will be described in detail with reference to FIG. 11C, which will be described below.

In Step S37, the imaging control unit 41 turns off the laser device 3 to turn off the marker.

In Step S38, the imaging control unit 41 determines whether to perform the next imaging operation. When the determination conditions are satisfied (Yes), the imaging control unit 41 returns to Step S31. When the determination conditions are not satisfied (No), the imaging control unit 41 ends the process shown in FIG. 11A.

FIG. 11B is a flowchart illustrating in detail the marker image processing in Step S35.

The imaging control unit 41 calls the marker image processing unit 42B and the marker image processing starts.

In Step S40, the marker image processing unit 42B extracts a marker pattern from the marker-given image group and generates a marker-extracted image group.

In Step S41, the marker image processing unit 42B calculates the correction parameters between the camera images from the marker pattern of the marker-extracted image group and ends the marker image processing shown in FIG. 11B.

FIG. 11C is a flowchart illustrating in detail the markerless image processing shown in Step S36.

The imaging control unit 41 calls the markerless image processing unit 43B and the markerless image processing starts.

In Step S42, the markerless image processing unit 43B applies the correction parameter to the markerless image group to generate one markerless composite image 77 (see FIG. 9E). When the process in Step S42 ends, the markerless image processing unit 43B ends the markerless image processing shown in FIG. 11C.

The plural camera images capturing and processing apparatus 1B according to the third embodiment captures a markerless image and then captures a marker-given image. However, the invention is not limited thereto. The plural camera images capturing and processing apparatus may capture a marker-given image and then capture a markerless image.

Effects of Third Embodiment

The above-described third embodiment has the following effects (E) and (F).

(E) The plural camera images capturing and processing apparatus 1B turns on the laser device 3B and captures a marker-given image group. In addition, the plural camera images capturing and processing apparatus 1B turns off the laser device 3B and captures a markerless image group. As such, the plural camera images capturing and processing apparatus 1B captures the marker-given image group and the markerless image group at different times. Therefore, it is possible to prevent a marker from being reflected in the markerless image group.

(F) The plural camera images capturing and processing apparatus 1B gives the markers using the visible-light laser device 3B. Therefore, it is possible to easily recognize the failure or adjustment error of the laser device 3B.

Fourth Embodiment

In this embodiment, an example of a process when a plural camera images capturing and processing apparatus 1B (see FIG. 8) is continuously moved will be described. The plural camera images capturing and processing apparatus 1B according to the fourth embodiment captures a markerless image two times and captures a marker-given image one time.

FIGS. 12A to 12G are diagrams illustrating a multi-camera imaging process in the fourth embodiment will be described.

FIG. 12A is a diagram a first markerless image group. Markerless images 71C-1 to 71C-3 in the first markerless image group are captured by cameras 2B-1 to 2B-3, respectively, when laser devices 3B-1 and 3B-2 do not operate. An imaging control unit 41 acquires the markerless images 71C-1 to 71C-3 from the cameras 2B-1 to 2B-3 and stores the acquired images in the storage unit 44.

FIG. 12B is a diagram illustrating a marker-given image group.

The cameras 2B-1 to 2B-3 capture marker-given images 72C-1 to 72C-3 in the marker-given image group, respectively, when the laser devices 3B-1 and 3B-2 radiate laser beams 51B and 52B. The imaging control unit 41 acquires the marker-given images 72C-1 to 72C-3 from the cameras 2B-1 to 2B-3 and stores the acquired images in the storage unit 44.

FIG. 12C is a diagram illustrating a marker-extracted image group.

In this embodiment, marker-extracted images 73-1 to 73-3 are the same as those in the first embodiment shown in FIG. 4C.

FIG. 12D is a diagram illustrating a second markerless image group.

Markerless images 74C-1 to 74C-3 in the second markerless image group are captured by the cameras 2B-1 to 2B-3, respectively, when the laser devices 3B-1 and 3B-2 do not operate. The imaging control unit 41 acquires the markerless images 74C-1 to 74C-3 from the cameras 2B-1 to 2B-3 and stores the acquired images in the storage unit 44.

FIG. 12E is a diagram illustrating a markerless composite image group.

Markerless composite images 75-1 to 75-3 are obtained by composing the markerless images 71C-1 to 71C-3 and the markerless images 74C-1 to 74C-3, respectively.

Figure 12F:
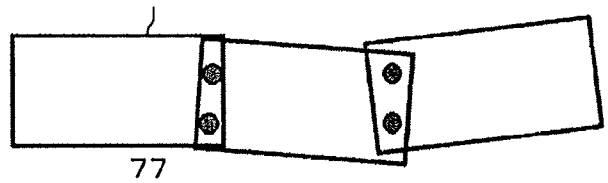

FIG. 12F is a diagram illustrating a marker-corrected image 76.

In this embodiment, the marker-corrected image 76 is the same as that in the first embodiment shown in FIG. 4D.

Figure 12G:
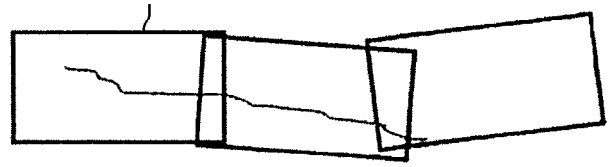

FIG. 12G is a diagram illustrating a markerless composite image 77. In this embodiment, the markerless composite image 77 is the same as that in the first embodiment shown in FIG. 4E.

FIGS. 13A to 13G are timing charts according to the fourth embodiment. In FIGS. 13A to 13G, the horizontal axis indicates time which is common to FIGS. 13A to 13G. Next, the timing charts will be described with reference to FIGS. 12A to 12G.

FIG. 13A is a diagram illustrating the presence and absence of the movement of the plural camera images capturing and processing apparatus 1B.

FIG. 13B is a diagram illustrating a camera imaging trigger.

FIG. 13C is a diagram illustrating a marker giving trigger.

FIG. 13D is a diagram illustrating an imaging time. The imaging time includes the processing time of the camera 2B.

FIG. 13E is a diagram illustrating a marker giving time.

FIG. 13F is a diagram illustrating marker image processing. A dashed line indicates the processing time of the camera 2. A solid line indicates the processing time of a marker image processing unit 42B of a control unit 4B.

FIG. 13G is a diagram illustrating markerless image processing. A dashed line indicates the processing time of the camera 2. A solid line indicates the processing time of a markerless image processing unit 43B of the control unit 4B.

The plural camera images capturing and processing apparatus 1B according to this embodiment is constantly moved in the depth direction.

At a time t1C, the imaging control unit 41 generates the camera imaging trigger. The cameras 2B-1 to 2B-3 capture the image of a lower surface 92. Then, an initial imaging period P1C-1 starts.

At a time t2C, the cameras 2B-1 to 2B-3 ends image processing and outputs markerless images 71C-1 to 71C-3. The imaging control unit 41 acquires the markerless images 71C-1 to 71C-3.

At a time t3C, the imaging control unit 41 generates the marker giving trigger and operates each laser device 3B. Each laser device 3B radiates visible laser beams 51B and 52B to the lower surface 92 of the concrete bridge 9.

At a time t4C, the imaging control unit 41 generates the camera imaging trigger. The cameras 2B-1 to 2B-3 capture the image of the lower surface 92 irradiated with the laser beams 51B and 52B.

At a time t5C, the cameras 2B-1 to 2B-3 end image processing and outputs marker-given images 72C-1 to 72C-3. The imaging control unit 41 acquires the marker-given images 72C-1 to 72C-3 and starts marker image processing shown in FIG. 12F. Then, an initial image processing period P2C-1 starts.

At a time t6C, the imaging control unit 41 generates the marker giving trigger and stops each laser device 3B.

At a time t7C, the imaging control unit 41 generates the camera imaging trigger. The cameras 2B-1 to 2B-3 capture the image of the lower surface 92.

At a time t8C, the marker image processing unit 42B ends the marker image processing and, calculates a correction parameter.

At a time t9C, the cameras 2B-1 to 2B-3 ends image processing, outputs markerless images 74C-1 to 74C-3, and end the initial imaging period P1C-1. The imaging control unit 41 acquires the markerless images 74C-1 to 74C-3. The markerless image processing unit 43B starts markerless image processing.

At a time t10C, the markerless image processing unit 43B ends the markerless image processing, generates a markerless composite image 77, and ends the initial image processing period P2C-1. The imaging control unit 41 starts a second imaging period P1C-2 after waiting for a time T and starts a second image processing period P2C-2 with the start of the second imaging period P1C-2.

Figure 14A:
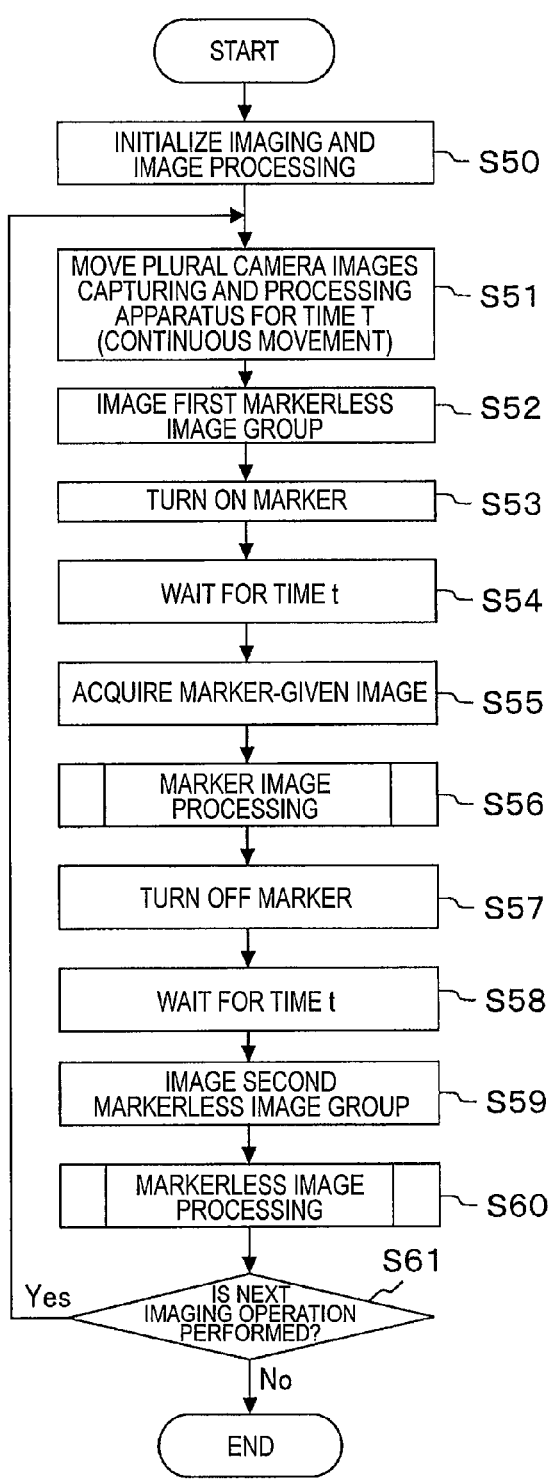
FIGS. 14A to 14C are flowcharts illustrating the multi-camera imaging process according to the fourth embodiment.
Figure 14B:
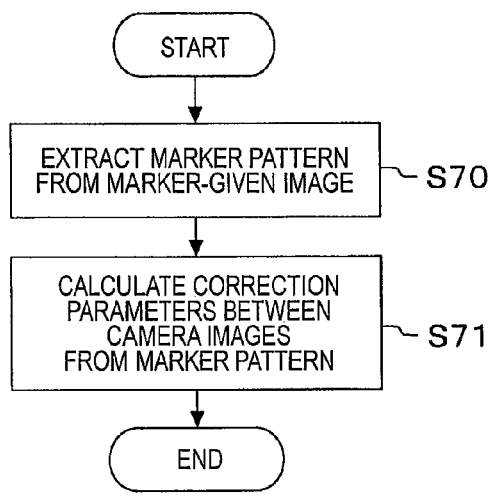
Figure 14C:
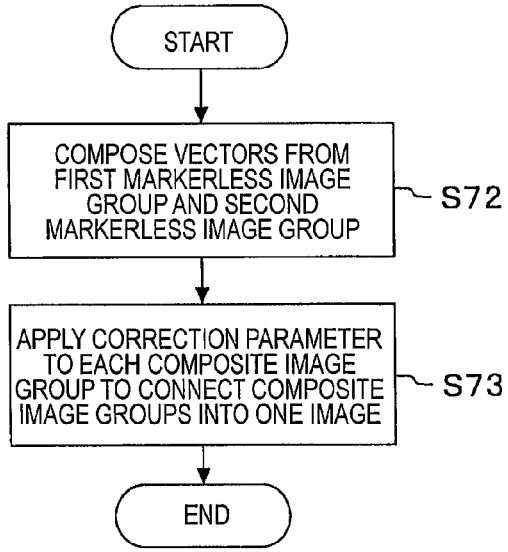

FIGS. 14A to 14C are flowcharts illustrating a multi-camera imaging process according to the fourth embodiment.

FIG. 14A is a flowchart illustrating the entire multi-camera imaging process.

When imaging starts, the plural camera images capturing and processing apparatus 1B starts the process shown in FIG. 14A.

In Step S50, the imaging control unit 41 initializes an imaging process and image processing.

In Step S51, the imaging control unit 41 directs the plural camera images capturing and processing apparatus 1B to wait for the time T and to be continuously moved. In this embodiment, the bridge inspection vehicle 8 supporting the plural camera images capturing and processing apparatus 1B constantly moves at a very low speed. First following flow proceeds at T=0.

In Step S52, the imaging control unit 41 instructs the cameras 2B-1 to 2B-3 to capture a first markerless image group. Here, the laser device 3B does not operate.

In Step S53, the imaging control unit 41 turns on a marker. The turn-on of the marker means that the laser device 3B radiates the laser beams 51B and 52B to the imaging region 6.

In Step S54, the imaging control unit 41 waits for the time t.

In Step S55, the imaging control unit 41 instructs the cameras 2B-1 to 2B-3 to capture a marker-given image group. At that time, the laser devices 3B-1 and 3B-2 operate.

In Step S56, the imaging control unit 41 performs marker image processing. The marker image processing will be described in detail with reference to the following FIG. 14B.

In Step S57, the imaging control unit 41 turns off the marker. The turn-off of the marker means that the laser device 3B stops an operation of radiating laser beams.

In Step S58, the imaging control unit 41 waits for the time t.

In Step S59, the imaging control unit 41 instructs the cameras 2B-1 to 2B-3 to capture a second markerless image group. Here, the laser device 3B does not operate.

In Step S60, the imaging control unit 41 instructs the markerless image processing unit 43B to perform markerless image processing. The markerless image processing will be described in detail with reference to the following FIG. 14C.

In Step S61, the imaging control unit 41 determines whether to perform the next imaging operation. When the determination conditions are satisfied (Yes), the imaging control unit 41 returns to the process in Step S51. When the determination conditions are not satisfied (No), the imaging control unit 41 ends the process shown in FIG. 14A.

FIG. 14B is a flowchart illustrating in detail the marker image processing in Step S56.

The imaging control unit 41 calls the marker image processing unit 42B and the marker image processing starts.

In Step S70, the marker image processing unit 42B extracts a marker pattern from the marker-given image group and generates a marker-extracted image group.

In Step S71, the marker image processing unit 42B calculates the correction parameters between the camera images from the marker pattern of the marker-extracted image group and ends the marker image processing shown in FIG. 14B.

FIG. 14C is a flowchart illustrating in detail the markerless image processing in Step S60.

In Step S72, the markerless image processing unit 43B performs vector composition to generate a markerless composite image from the first markerless image group and the second markerless image group. Hereinafter, in some cases, the composition of vectors from two similar images is referred to as the interpolation of two images.

In Step S73, the markerless image processing unit 43B applies the correction parameter to each markerless composite image to generate one markerless composite image 77. When the process in Step S72 ends, the markerless image processing unit 43B ends the markerless image processing shown in FIG. 14C.

The plural camera images capturing and processing apparatus 1B according to the fourth embodiment captures the first markerless image group in the first imaging operation, captures the marker-given image group in the second imaging operation, and captures the second markerless image group in the third imaging operation. However, the invention is not limited thereto. The plural camera images capturing and processing apparatus 1B may capture the first marker-given image group in the first imaging operation, capture the markerless image in the second imaging operation, and capture the second marker-given image group in the third imaging operation. Since the first marker-given image group and the second marker-given image group are captured, the marker is less likely to be concealed by the unevenness of the surface of the object to be captured. Therefore, it is possible to accurately calculate the correction parameter and to connect the markerless image groups, without an error.

When an adhesive droplet marker 3D according to a fifth embodiment, which will be described below, is used instead of the laser device 3B according to the fourth embodiment, a markerless image group may be captured first, a marker-given image group having a droplet marker attached thereto may be captured after the next time t and after the time t after next, and the correction parameter may be extrapolated from the marker-given image group at an initial imaging time.

Effects of Fourth Embodiment

The above-described fourth embodiment has the following effect (G).

(G) The plural camera images capturing and processing apparatus 1B captures a plurality of markerless images and composes the markerless images. Therefore, it is possible to acquire images at a marker giving time and connect the images to generate a composite image.

Fifth Embodiment

As in the first to fourth embodiments, in the method of using the laser beam as a standard for connecting the images, the images which are captured at different times by the camera which is moving do not have a common marker and it is difficult to connect these images. In this embodiment, the structure and process of an imaging apparatus which captures a plurality of images of cracks in the moving direction and generates a composite image will be described.

Figure 15:
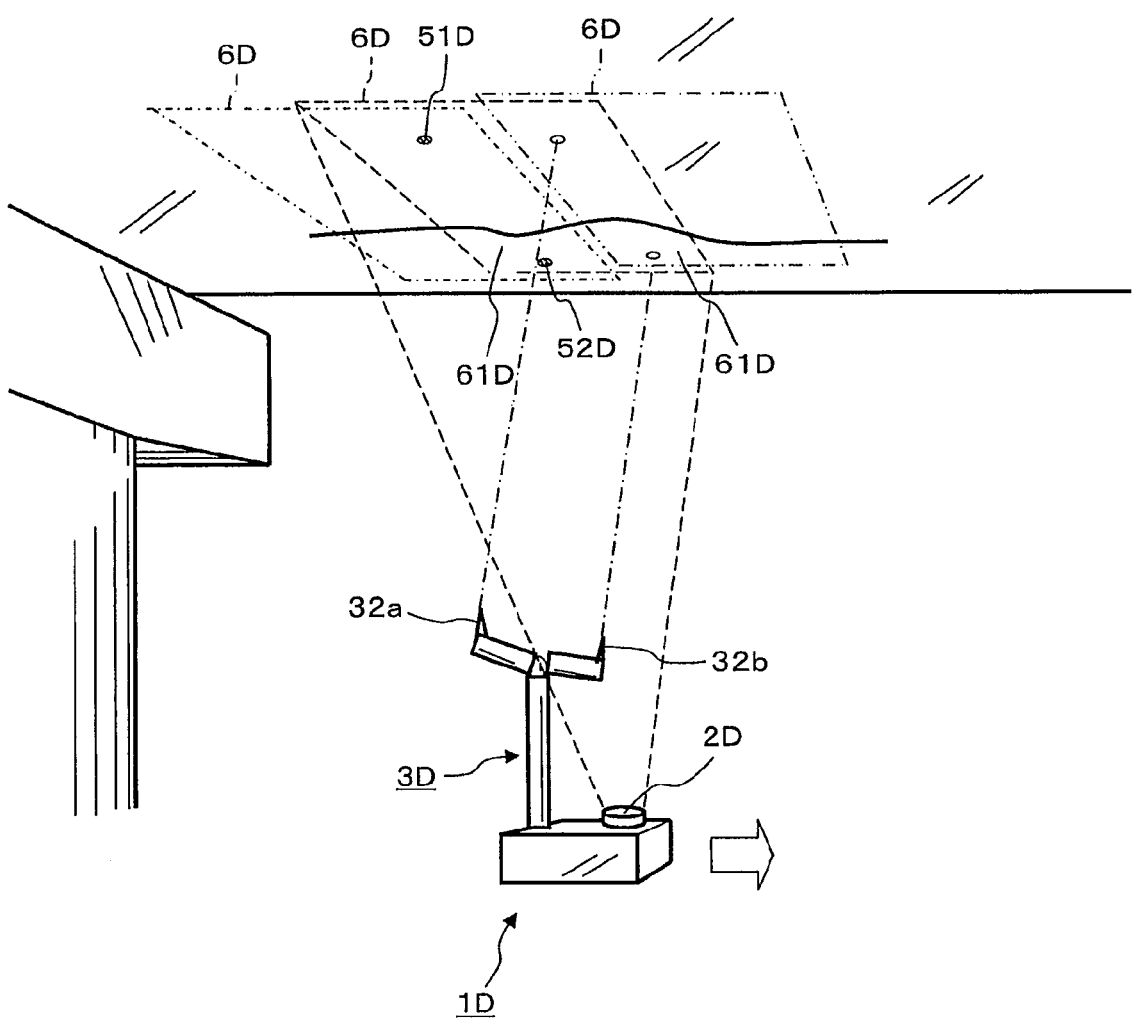
FIG. 15 is a diagram illustrating the outward appearance and operation of a plural camera images capturing and processing apparatus according to a fifth embodiment.

FIG. 15 is a diagram illustrating the outward appearance and operation of a plural camera images capturing and processing apparatus 1D according to a fifth embodiment.

The plural camera images capturing and processing apparatus 1D includes a camera 2D (imaging means) and an adhesive droplet marker 3D (marker giving means). The plural camera images capturing and processing apparatus 1D is supported by, for example, a bridge inspection vehicle 8 (not shown; see FIG. 1A) and is slowly moved to the right direction of FIG. 15.

The camera 2D captures the image of an imaging region 6D. The adhesive droplet marker 3D attaches two droplet markers 51D and 52D (adhesive markers) to the first half of the imaging region 6D through two nozzles 32a and 32b. The first half of the imaging region 6D is a common imaging region 61D in which the imaging region 6D and the next imaging region 6D overlap each other.

Figure 16:
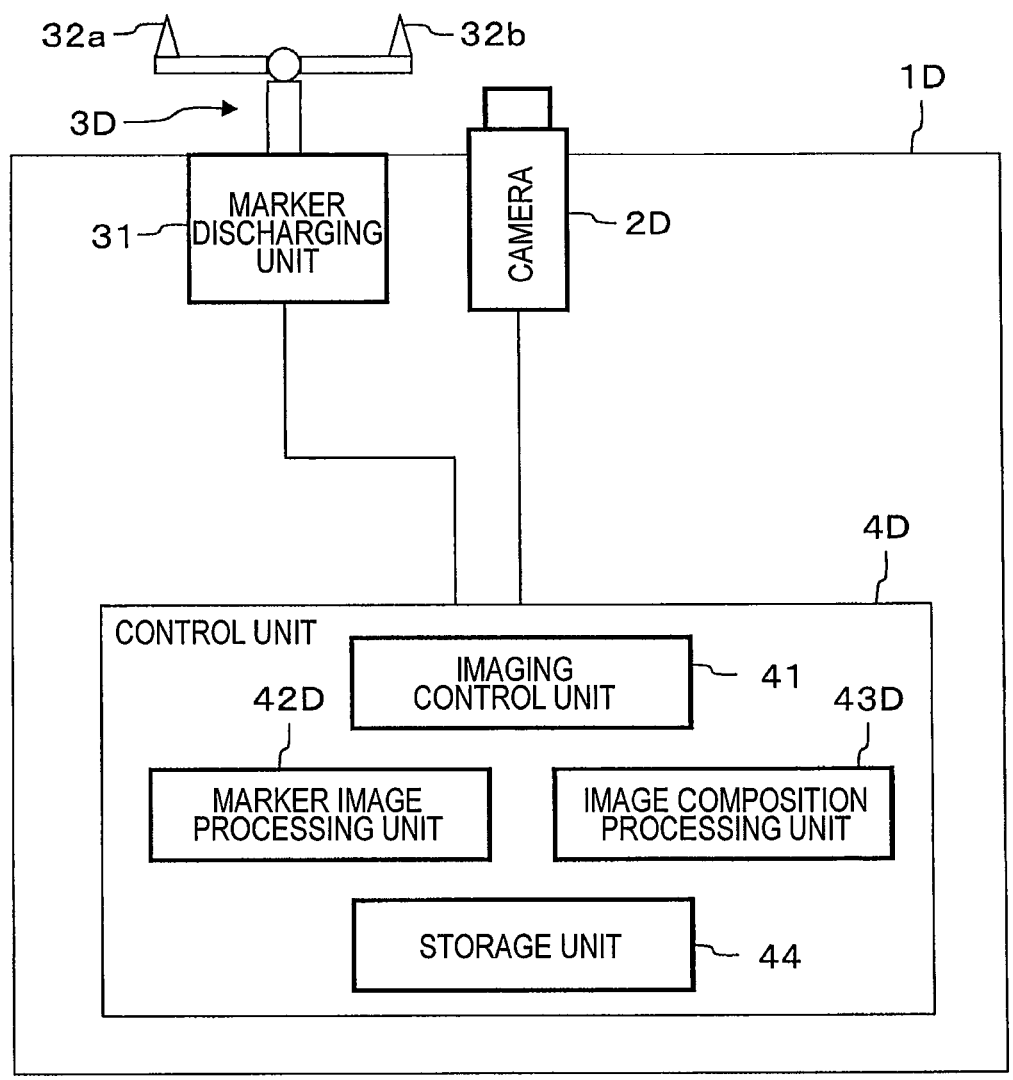
FIG. 16 a diagram schematically illustrating the structure of the plural camera images capturing and processing apparatus according to the fifth embodiment.

FIG. 16 is a diagram schematically illustrating the structure of the plural camera images capturing and processing apparatus 1D according to the fifth embodiment.

The plural camera images capturing and processing apparatus 1D includes the camera 2D, the adhesive droplet marker 3D (marker giving means), and a control unit 4D which is connected to the camera 2D and the adhesive droplet marker 3D.

The camera 2D captures images in the upward direction in order to capture the image of a lower surface 92 of a concrete bridge 9. The camera 2D can capture, for example, a visible light image.

The adhesive droplet marker 3D includes a marker discharging unit 31 and two nozzles 32a and 32b. The adhesive droplet marker 3D discharges a marker solution from the marker discharging unit 31 through the nozzles 32a and 32b and attaches two droplet markers 51D and 52D, which are adhesive markers, to the first half of the imaging region 6D in the moving direction.

The control unit 4D includes an imaging control unit 41 (control means), a marker image processing unit 42D (correction parameter calculation means), an image composition processing unit 43D (image composition means), and a storage unit 44.

The imaging control unit 41 (control means) controls the camera 2D and the adhesive droplet marker 3D to capture a markerless image in which the droplet markers 51D and 52D are not given to the first half of the imaging region 6D in the moving direction and a marker-given image in which the droplet markers 51D and 52D are given to the first half of the imaging region 6D in the moving direction. The images acquired by the imaging control unit 41 are stored in the storage unit 44.

The marker image processing unit 42D (correction parameter calculation means) calculates a correction parameter, which is information for aligning the inclinations, sizes, and positions of the imaging region 6D before movement and the imaging region 6D after movement, on the basis of each markers given to the image group acquired by the imaging control unit 41.

The image composition processing unit 43D (image composition means) generates a markerless composite image in which the droplet markers 51D and 52D are not given, on the basis of the correction parameter.

The storage unit 44 is, for example, flash memory or an HDD and stores digital data which is typified by an image.

FIGS. 17A to 17C-3 are diagrams illustrating a multi-camera imaging process according to the fifth embodiment.

Figure 17A:
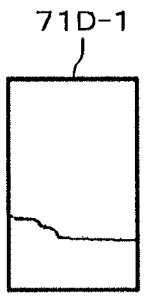
FIGS. 17A to 17C-3 are diagrams illustrating a multi-camera imaging process according to the fifth embodiment.

FIG. 17A is a diagram illustrating an image 71D-1 which is first captured.

The image 71D-1 is captured by the camera 2D before the adhesive droplet marker 3D is operated.

Figures 1, 17B:
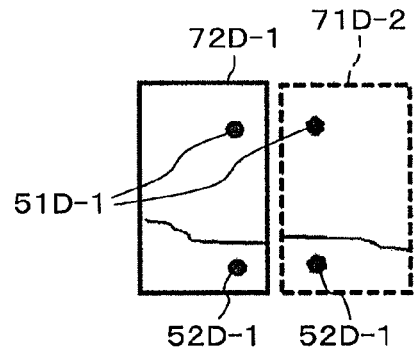
Figures 2, 17B:
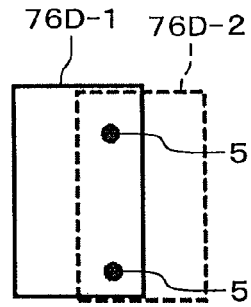

FIG. 17B-1 is a diagram an image 72D-1 and an image 71D-2.

The image 72D-1 is captured by the camera 2D at the position where the image 71D-1 is captured when the droplet markers 51D-1 and 52D-1 are attached.

The image 71D-2 is captured by the camera 2D when the droplet markers 51D-1 and 52D-1 are moved to the second half of the imaging region in the moving direction by the movement of the plural camera images capturing and processing apparatus 1D.

FIG. 17B-2 is a diagram illustrating the connection of the marker-extracted image 76D-1 and 76D-2.

Since the same droplet markers 51D-1 and 52D-1 are included in the marker-extracted image 76D-1 and 76D-2, the marker-extracted image 76D-1 and 76D-2 are processed to connect each other on the basis of the markers, 51D-1 and 52D-1, to overlap and it is possible to calculate the correction parameter.

Figures 3, 17B:

FIG. 17B-3 is a diagram illustrating a composite image of the image 71D-1 and the image 71D-2.

The image 71D-2 and the image 71D-1 are connected to each other on the basis of the correction parameter to generate a markerless composite image 77D-1.

Figures 1, 17C:
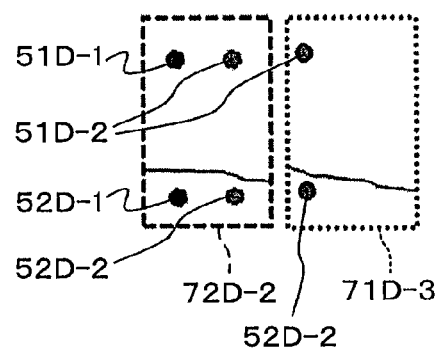
Figures 2, 17C:
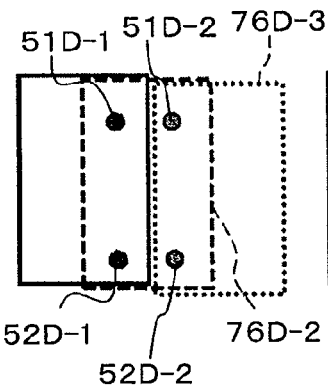
Figures 3, 17C:

FIG. 17C-1 is a diagram illustrating an image 72D-2 and an image 71D-3.

The image 72D-2 is captured by the camera 2D at the position where the image 71D-2 is captured when the droplet markers 51D-2 and 52D-2 are attached.

The image 71D-3 is captured by the camera 2D when the droplet markers 51D-2 and 52D-2 are moved to the second half of the imaging region in the moving direction by the movement of the plural camera images capturing and processing apparatus 1D.

FIG. 17C-2 is a diagram illustrating the connection of the maker-extracted image 76D-2 and 76D-3.

Since the same droplet markers 51D-2 and 52D-2 are included in the marker-extracted image 76D-2 and 76D-3, the marker-extracted image 76D-2 and the image 76D-3 are processed to connect each other on the basis of the markers, 51D-2 and 52D-2 to overlap and it is possible to calculate the correction parameter.

FIG. 17C-3 is a diagram illustrating a composite image of the images 71D-1 to 71D-3.

The images 71D-1 to 71D-3 are connected to each other on the basis of each correction parameter to generate a markerless composite image 77D-2.

FIGS. 18A to 18H are timing charts according to the fifth embodiment. In FIGS. 18A to 18H, the horizontal axis indicates time which is common to FIGS. 18A to 18H. Next, the timing charts will be described with reference to FIGS. 15 to 17C-3.

FIG. 18A is a diagram illustrating the presence and absence of the movement of the plural camera images capturing and processing apparatus 1D.

FIG. 18B is a diagram illustrating a camera imaging trigger.

FIG. 18C is a diagram illustrating a marker giving trigger.

FIG. 18D is a diagram illustrating an imaging time. The imaging time includes the processing time of the camera 2D. The first image is A and the second image is B in each imaging period.

FIG. 18E is a diagram illustrating the presence and absence of a droplet marker in the first half of the imaging region 6D in the moving direction.

FIG. 18F is a diagram illustrating the presence and absence of a droplet marker in the second half of the imaging region 6D in the moving direction. FIG. 18G is a diagram illustrating marker image processing B which calculates the correction parameters with second image B in the previous imaging period and first image A in the current imaging period. A thick dashed line indicates the calculation time. A thin dashed line indicates the processing time of the camera 2D.

FIG. 18H is a diagram illustrating marker image processing A which composes images with the first image A in the previous imaging period and the first image A in the current imaging period. A thick dashed line indicates an image composition time. A thin dashed line indicates the processing time of the camera 2D. A solid line indicates the processing time of the marker image processing unit 42D.

The plural camera images capturing and processing apparatus 1D according to this embodiment is stopped at a time t1D. When imaging ends, the plural camera images capturing and processing apparatus 1D moves a distance corresponding to half of the imaging region 6D in the depth direction until the next imaging operation starts.

At a time t1D, the imaging control unit 41 generates the camera imaging trigger. The camera 2D captures the image of the lower surface 92. Then, an initial imaging period P1D-1 starts.

At a time t2D, the camera 2D ends image processing and outputs the image 71D-1. The imaging control unit 41 acquires the image 71D-1.

At a time t3D, the imaging control unit 41 generates the marker giving trigger and operates the adhesive droplet marker 3D. The adhesive droplet marker 3D discharges the marker solution to attach two droplet markers 51D and 52D to the lower surface 92 of the concrete bridge 9.

At a time t4D, the imaging control unit 41 generates the camera imaging trigger. The camera 2D captures the image of the lower surface 92 to which the droplet markers 51D and 52D are attached.

At a time t5D, the camera 2D ends image processing and outputs the image 72D-1. The imaging control unit 41 acquires the image 72D-1. Then, the initial imaging period P1D-1 ends. The camera 2D is slowly moved for the time T from the first imaging period to the second imaging period. The, two droplet markers 51D and 52D are moved from the first half to the second half of the imaging region 6.

At a time t6D, the imaging control unit 41 generates the camera imaging trigger. The camera 2D captures the image of the lower surface 92. Then, a second imaging period P1D-2 starts.

At a time t7D, the camera 2D ends image processing and outputs the image 71D-2. The imaging control unit 41 acquires the image 71D-2, starts the marker image processing B, and connects the image 72D-1 and the image 71D-2. Then, a second image processing period P2D-2 starts. When the marker image processing B ends, the imaging control unit 41 starts the marker image processing A.

At a time t8D, the imaging control unit 41 generates the marker giving trigger and operates the adhesive droplet marker 3D. The adhesive droplet marker 3D discharges the marker solution to attach two droplet markers 51D and 52D to the lower surface 92 of the concrete bridge 9.

At a time t9D, the imaging control unit 41 generates the camera imaging trigger. The camera 2D captures the image of the lower surface 92 to which the droplet markers 51D and 52D are attached.

At a time t10D, the camera 2D ends image processing and outputs the image 72D-2. The imaging control unit 41 acquires the image 72D-2. Then, the second imaging period P1D-2 ends. The camera 2D is slowly moved until a third imaging period P1D-3.

At a time t11D, the imaging control unit 41 ends the marker image processing A and outputs the connected markerless composite image 77D-1. Then, the second image processing period P2D-2 ends.

Similarly, the process from the time t6D to the time t11D is performed and the camera is slowly moved for the time T until the next imaging period. In this way, it is possible to obtain correction parameters and a composite image in which the images are connected to each other in the traveling direction.

Figure 19A:
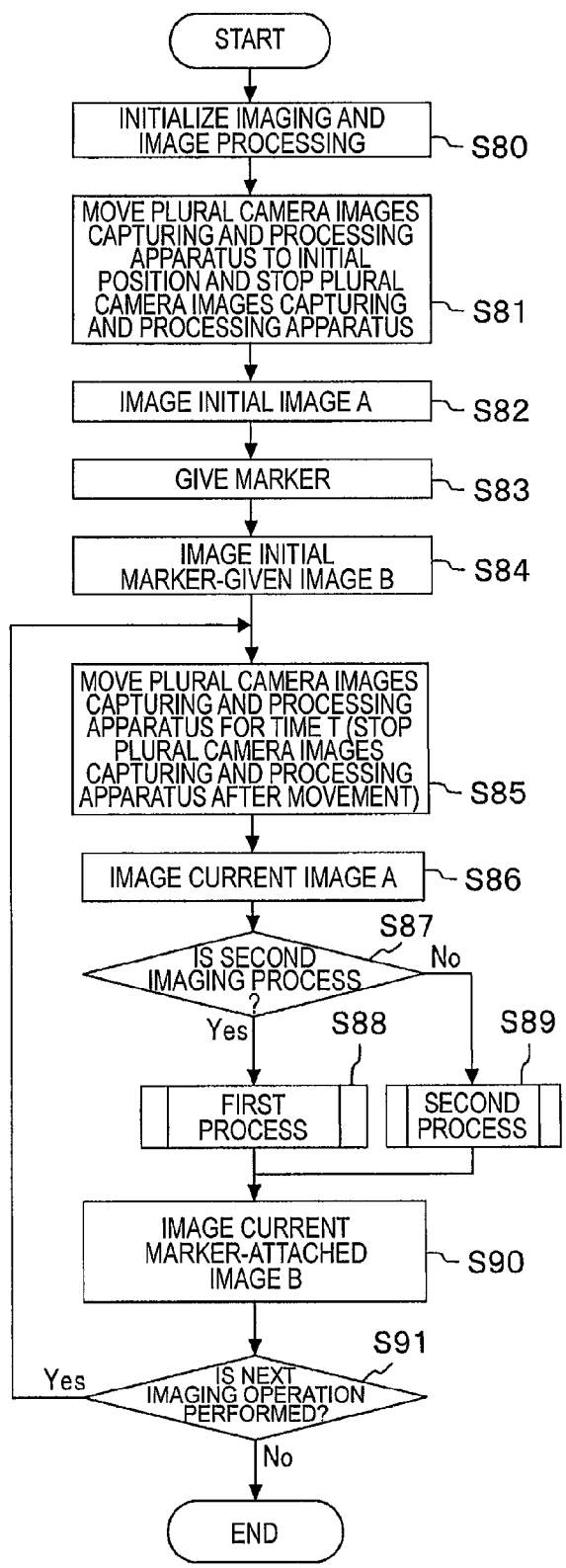
FIGS. 19A to 19C are flowcharts illustrating an imaging process according to the fifth embodiment.
Figure 19B:
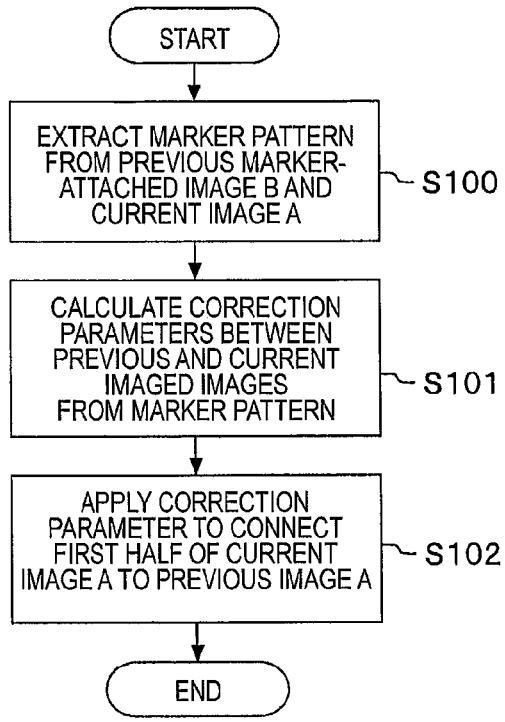
Figure 19C:
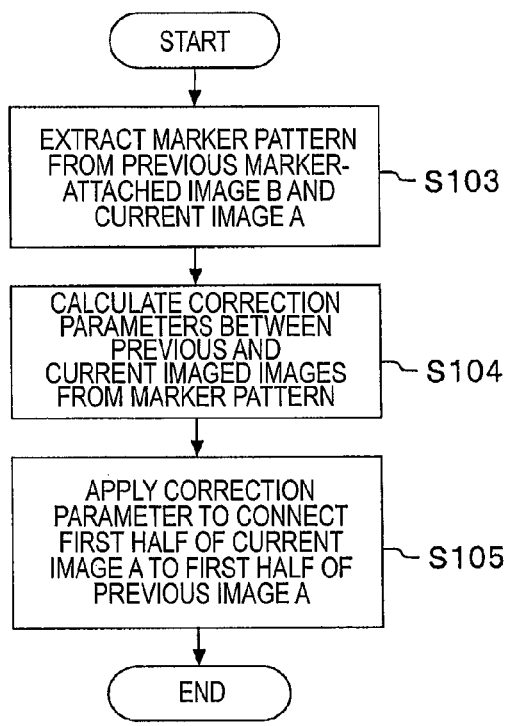

FIGS. 19A to 19C are flowcharts illustrating an imaging process according to the fifth embodiment.

FIG. 19A is a flowchart illustrating the entire multi-camera imaging process.

When imaging starts, the plural camera images capturing and processing apparatus 1D starts the process shown in FIG. 19A.

In Step S80, the imaging control unit 41 initializes the imaging process and image processing.

In Step S81, the bridge inspection vehicle 8 (see FIGS. 1A and 1B) supporting the plural camera images capturing and processing apparatus 1B is moved to a predetermined position and is then stopped.

In Step S82, the imaging control unit 41 instructs the camera 2D to capture a first image A. The image A means an image in which no marker is given to at least the first half in the moving direction.

In Step S83, the imaging control unit 41 instructs the marker discharging unit 31 to given markers. The term "giving of the markers" means that the adhesive droplet marker 3D discharges a marker solution to attach two droplet markers 51D and 52D to the imaging region 6.

In Step S84, the imaging control unit 41 instructs the camera 2D to capture a first marker-given image B. The marker-given image B means an image in which markers are given to the first half in the moving direction.

In Step S85, the bridge inspection vehicle 8 (see FIGS. 1A and 1B) supporting the plural camera images capturing and processing apparatus 1B is moved for the time T and is then stopped.

In Step S86, the imaging control unit 41 instructs the camera 2D to capture the current image A.

In Step S87, the imaging control unit 41 determines whether the imaging operation is a second process. When the determination conditions are satisfied (Yes), the imaging control unit 41 performs the process in Step S88. When the determination conditions are not satisfied (No), the imaging control unit 41 performs the process in Step S89.

In Step S88, the imaging control unit 41 performs the first process shown in FIG. 19B using the marker image processing unit 42D and the image composition processing unit 43D and then performs the process in Step S90.

In Step S89, the imaging control unit 41 performs the second process shown in FIG. 19C using the marker image processing unit 42D and the image composition processing unit 43D.

In Step S90, the imaging control unit 41 instructs the camera 2D to capture the current marker-attached image B.

In Step S91, the imaging control unit 41 determines whether to perform the next imaging operation. When the determination conditions are satisfied (Yes), the imaging control unit 41 returns to the process in Step S85. When the determination conditions are not satisfied (No), the imaging control unit 41 ends the process shown in FIG. 19A.

FIG. 19B is a flowchart illustrating in detail the first process in Step S88.

The imaging control unit 41 calls the marker image processing unit 42D and the image composition processing unit 43D and the first process starts.

In Step S100, the marker image processing unit 42D extracts a marker pattern from the previous marker-attached image B and the current image A and generates a marker-extracted image group.

In Step S101, the marker image processing unit 42D calculates the correction parameters between the camera images from the marker pattern.

In Step S102, the image composition processing unit 43D applies the correction parameter to connect the first half of the current image A to the previous image A, thereby generating a markerless composite image. When the process in Step S102 ends, the image composition processing unit 43D ends the first process shown in FIG. 19B.

FIG. 19C is a flowchart illustrating in detail the second process in Step S89.

The imaging control unit 41 calls the marker image processing unit 42D and the image composition processing unit 43D and the second process starts.

In Step S103, the marker image processing unit 42D extracts a marker pattern from the previous marker-attached image B and the current image A and generates a marker-extracted image group.

In Step S104, the marker image processing unit 42D calculates the correction parameters between the camera images from the marker pattern of the marker-extracted image group.

In Step S105, the image composition processing unit 43D applies the correction parameter to connect the first half of the current image A to the first half of the previous image A, thereby generating a composite image to which no marker is given. When the process in Step S105 ends, the image composition processing unit 43D ends the second process shown in FIG. 19C.

In the fifth embodiment, the droplet markers 51D and 52D are marking materials which are attached to the object to be captured for a long time or a short time. In addition, the marker may not be a droplet, but may be, for example, an adhesive solid material.

When the marker is a volatile droplet or a sublimable solid, it is removed after imaging and does not cause any problem in the next inspection. When the marker is a non-volatile liquid or a non-sublimable solid, it remains for a long time and is likely to cause problems in the next inspection. Therefore, the plural camera images capturing and processing apparatus 1D may use a material which is removed in an inspection period or a material which is detached from the object to be captured. For example, since bridge inspection is performed every five years, a material which is removed or detached from the object to be captured within five years may be used as the marker.

Effects of Fifth Embodiment

The above-described fifth embodiment has the following effects (H) and (I).

(H) The plural camera images capturing and processing apparatus 1D attaches the droplet markers 51D and 52D to the lower surface 92 which is the object to be captured. Therefore, the plural camera images capturing and processing apparatus 1D can capture a plurality of images whenever it moves and can calculate the correction parameter between adjacent captured images on the basis of the droplet markers 51D and 52D.

(I) The plural camera images capturing and processing apparatus 1D captures the image of the same imaging region before and after it attaches the droplet markers 51D and 52D. Therefore, the plural camera images capturing and processing apparatus 1D can generate a composite image of portions to which no marker is given in adjacent captured images on the basis of the correction parameter between the adjacent captured images.

(Marker Pattern Identification Conditions)

Next, conditions for identifying a marker pattern from a captured image will be described. The marker pattern may be a laser marker, a droplet marker, or a solid-state marker.

One of the marker pattern conditions is a shape. The term "shape" includes, for example, point shapes, linear shapes (straight lines or curves), circular shapes, and polygonal shapes, such as rectangular shapes, diamond shapes, triangular shapes, and bird shapes, with different sizes or directions. In this case, the marker pattern is identified by determining whether the shape of the marker in the captured image is identical to a predetermined shape.

One of the marker pattern conditions is a position. The term "position" means, for example, the order of a specific number of marker patterns from the end. In this case, the marker pattern is identified by determining the order of the marker pattern from the end.

One of the marker pattern conditions is a plurality of points or lines or an arbitrary shape. In this case, in a row of at least two or more pattern in the direction of the captured image or a row of three or more patterns in an arbitrary direction, arrangement, a direction, an interval, or a size (including the length of a line) for limiting the number of patterns in the row is determined to identify the marker pattern.

One of the marker pattern conditions is the kind of color or light. The term "kind of light" includes, for example, visible light, infrared rays, and ultraviolet rays. In this case, the marker pattern is identified by identifying the kind of color or light of the marker pattern or by a camera which captures only the kind of predetermined color or light.

The marker pattern may be a combination of these conditions. The marker pattern identification conditions are shown in the following Table 1.

TABLE 1

| Marker pattern conditions | Marker pattern identification method |
|---|---|
| Shape (point, line, circle, rectangle, diamond, triangle, bird, . . . ) | Determine whether the shape of a marker pattern is identical to a predetermined shape |
| Position (specific number of marker patterns) | The order of a specific number of marker patterns from the end |
| A plurality of points or lines, or an arbitrary shape | Arrangement, direction, interval, or size (including the length of a line) for limiting the number of marker patterns arranged in a row |

TABLE 1-continued

| Marker pattern conditions | Marker pattern identification method |
|---|---|
| Kind of color or light (visible light/infrared rays/ultraviolet rays) | Brightness of each kind of color or light of marker pattern |

(Image Adjustment Elements and Marker Patterns)

Next, each image adjustment element, marker pattern conditions for implementing the image adjustment elements, and an image adjustment process will be described.

When the image adjustment element is the rotation or inclination of an image, the marker pattern conditions in a common region are two or more spots or one or more lines which can be specified. Two or more spots mean two points or two points which can be specified in a predetermined shape.

When the marker pattern conditions are two or more spots, the image adjustment process aligns the inclination of two adjacent images such that the directions of two spots which are common to the two adjacent images are aligned with each other.

When the marker pattern conditions are one or more lines which can be specified, the image adjustment process aligns the inclination of two adjacent images such that the directions of one line common to the two adjacent images are aligned with each other.

When the image adjustment element is the magnification or dimensions of an image, the marker pattern conditions in the common region are two or more spots or one or more shapes with a length which can be specified. The two or more spots mean two points or two points which can be specified in a predetermined shape. The one or more shapes with a length which can be specified mean an arbitrary shape including a line whose length has been known.

When the marker pattern conditions are two or more spots, the magnification of two adjacent images is adjusted such that the intervals between two spots common to the two adjacent images are equal to each other.

When the marker pattern conditions are one or more shapes with a length which can be specified 1, the magnification of two adjacent images is adjusted such that the specified lengths of the marker common to the two adjacent images are equal to each other.

When the image adjustment element is a vertical position or a position in the up-down direction, the marker pattern conditions in the common region are one or more spots or lines. The image adjustment process is performed by adjusting the vertical positions of two images such that the vertical positions of a specified marker pattern are aligned with each other.

When the image adjustment element is a horizontal position or a position in the left-right direction, the marker pattern conditions in the common region are one or more spots or lines. The image adjustment process is performed by adjusting the horizontal positions of two images such that the horizontal positions of a specified marker pattern are aligned with each other.

The image adjustment elements, the marker pattern conditions, and the image adjustment process are shown in the following Table 2.

The marker is concealed by the unevenness of the object to be captured. Therefore, it is preferable to set the marker pattern such that the number of markers greater than necessary is included in the common region between two adjacent images.

TABLE 2

| Image adjustment element | Marker pattern conditions in common region | Image adjustment process after marker pattern is specified |
|---|---|---|
| Rotation (inclination) | Two or more spots (two points or two points which can be specified in a specific shape) | The inclination of two adjacent images is adjusted such that the directions of two spots common to the two adjacent images are aligned with each other |
| | One or more lines which can be specified | The inclination of two adjacent images is adjusted such that the directions of one line common to the two adjacent images are aligned with each other |
| Magnification (dimensions) | Two or more spots (two points or two points which can be specified in a specific shape) | The magnification of two adjacent images is adjusted such that the intervals between two spots common to the two adjacent images are equal to each other |
| | One or more shapes with a length which can be specified (line with a length which has been known or an arbitrary shape including a line) | The magnification of two adjacent images is adjusted such that the specified lengths of the marker common to the two adjacent images are equal to each other |
| Vertical position (up-down direction) | One or more spots or lines | The vertical positions of two images are adjusted such that the vertical positions of a specified marker pattern are aligned with each other |
| Horizontal direction (left-right direction) | One or more spots or lines | The horizontal positions of two images are adjusted such that the horizontal positions of a specified marker pattern are aligned with each other |

Sixth Embodiment

In the plural camera images capturing and processing apparatus 1 according to the first to fourth embodiments shown in FIGS. 1A and 1B, each imaging region 6 is relatively changed by, for example, an error in the attachment angle or position of each camera 2 or each laser device 3 and the shaking of each camera 2 or each laser device 3 during movement. It is necessary to extend an overlap portion between the imaging regions 6 in order to reliably irradiate the common imaging region 61 with laser beams (spots). In this case, the number of cameras 2 needs to be increased.

In a method of radiating a large number of spot beams or a method of radiating a large number of line beams, it is also possible to reliably irradiate the common imaging region 61. However, when a simple spot beam or a simple line beam is used, it is difficult to identify each marker. Therefore, it is difficult to apply, for example, the rotation, the magnification, the vertical position, and the horizontal position shown in Table 2 to the image adjustment elements.

In this embodiment, for laser beams, one line beam and a plurality of spot beams are asymmetrically combined with each other to identify each marker.

Figure 20:
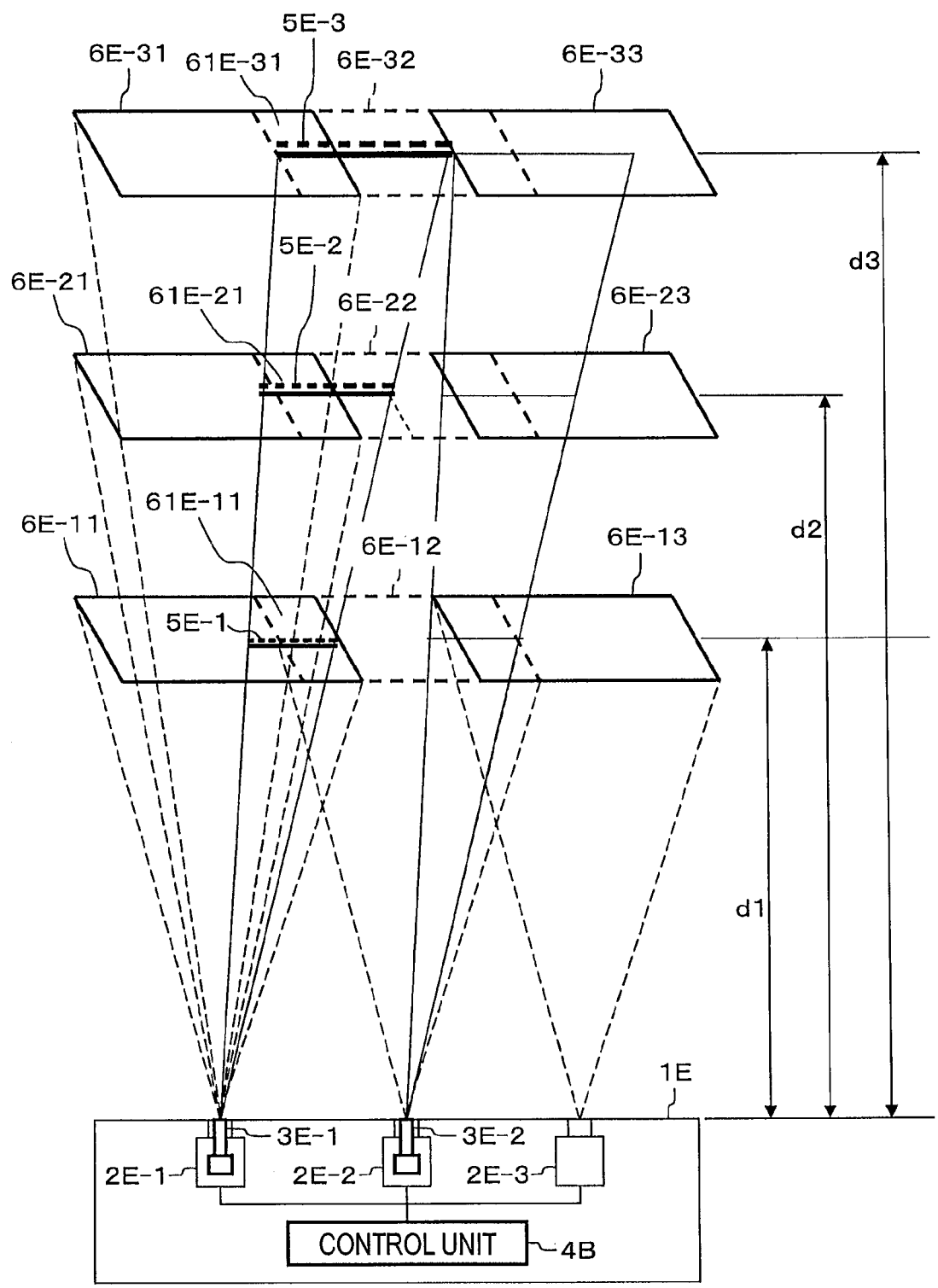
FIG. 20 is a diagram illustrating a plural camera images capturing and processing apparatus according to a sixth embodiment.

FIG. 20 is a diagram illustrating a plural camera images capturing and processing apparatus 1E according to a sixth embodiment.

The plural camera images capturing and processing apparatus 1E according to the sixth embodiment includes at least three cameras 2E-1 to 2E-3, laser devices 3E-1 and 3E-2, and a control unit 4B. Hereinafter, when the cameras 2E-1 to 2E-3 are not particularly distinguished from each other, they are simply referred to as cameras 2E. When the laser devices 3E-1 and 3E-2 are not particularly distinguished from each other, they are simply referred to as laser devices 3E.

The cameras 2E-1 to 2E-3 each includes a distance measurement sensor (not shown) which measures the distance to an object to be captured (for example, the lower surface 92 shown in FIGS. 1A and 1B) and a zoom mechanism (not shown). The laser device 3E-1 is provided integrally with the camera 2E-1. The laser device 3E-2 is provided integrally with the camera 2E-2. This structure makes it possible to reduce the number of processes for setting or positioning each camera 2E and each laser device 3E.

The camera 2E measures the distance to the object to be captured using the distance measurement sensor and controls the zoom mechanism such that the same range (the same area) of the object is constantly captured. Therefore, it is possible to capture the image of the surface of the object with the same resolution, regardless of the distance to the object.

A minimum object distance d1 is the minimum distance at which the plural camera images capturing and processing apparatus 1E can capture the image of the object. A maximum object distance d3 is the maximum distance at which the plural camera images capturing and processing apparatus 1E can capture the image of the object.

The images of imaging regions 6E-11 to 6E-13 at the minimum object distance d1 are captured by the cameras 2E-1 to 2E-3, respectively. Adjacent imaging regions 6E-11 and 6E-12 overlap each other and the overlap region is a common imaging region 61E-11. A laser marker 5E-1 is formed by one straight line and eight spots and is radiated to the common imaging region 61E-11. The eight spots of the laser marker 5E-1 are arranged so as to be equidistant from one straight line and are arranged such that the interval between the spots increases toward the right end. The right end of the laser marker 5E-1 is set so as to be aligned with the right end of the imaging region 6E-11.

Each laser device 3E radiates at least two spots to the common imaging region 61E-11 and radiates at least one spot to the imaging regions 6E-11 and 6E-12 outside the common imaging region 61E-11. The vertical position, horizontal position, rotation, and magnification of adjacent imaging regions 6E-11 and 6E-12 can be adjusted by the two spots radiated to the common imaging region 61E-11. The one or more spots radiated to the imaging regions 6E-11 and 6E-12 provide for the case in which the irradiation position of the laser marker 5E-1 deviates.

The images of imaging regions 6E-21 to 6E-23 at the distance d2 are captured by the cameras 2E-1 to 2E-3. Adjacent imaging regions 6E-21 and 6E-22 overlap each other and the overlap region is a common imaging region 61E-21. A laser marker 5E-2 is formed by one straight line and eight spots and is radiated to the common imaging region 61E-21.

The images of imaging regions 6E-31 to 6E-33 at the maximum object distance d3 are captured by the cameras 2E-1 to 2E-3, respectively. Adjacent imaging regions 6E-31 and 6E-32 overlap each other and the overlap region is a common imaging region 61E-31. A laser marker 5E-3 is formed by one straight line and eight spots and is radiated to the common imaging region 61E-31. The right end of the laser marker 5E-3 is set so as not to be radiated to the imaging region 6E-33. Since the laser marker 5E-3 is not radiated to an adjacent common imaging region 61E-32, the plural camera images capturing and processing apparatus 1E can compose the captured image group into one high-resolution image.

Hereinafter, when the laser markers 5E-1 to 5E-3 are not particularly distinguished from each other, they are simply referred to as laser markers 5E. When the common imaging regions 61E-11, 61E-21, and 61E-31 are not particularly distinguished from each other, they are simply referred to as common imaging regions 61E.

The laser device 3E radiates laser beams at a predetermined angle. When the distance from the laser device 3E to the object is changed, positional deviation occurs between the irradiated marker position and the common imaging region 61E of the camera 2E and the marker is likely to interfere with the marker in an adjacent common imaging region 61E. This embodiment solves these problems.

FIGS. 21A to 21E are diagrams illustrating an image adjustment process according to the sixth embodiment.

Figure 21B:
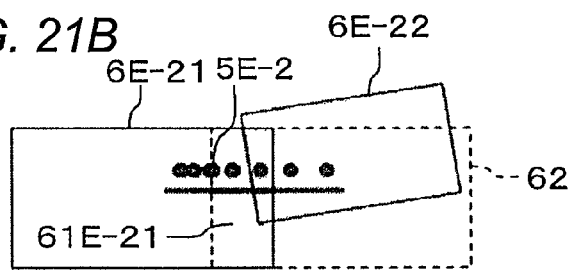
FIGS. 21A to 21E are diagrams illustrating an image adjustment process according to the sixth embodiment.
Figure 21A:
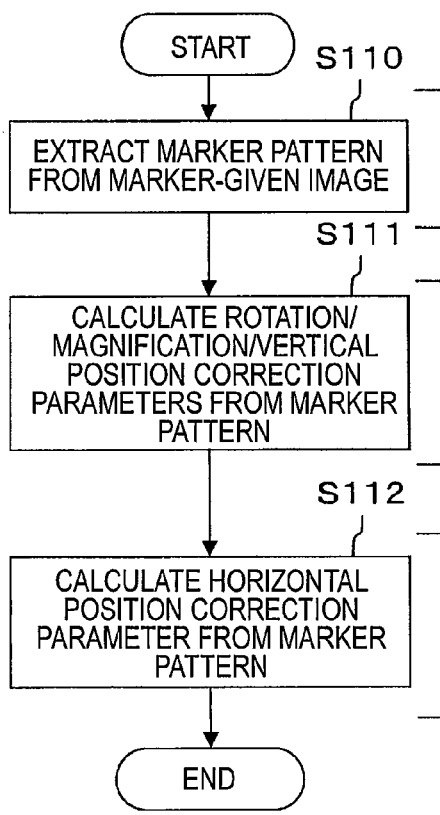

FIG. 21A is a flowchart illustrating the image adjustment process.

When a marker-given image group is captured, a marker image processing unit 42B (see FIG. 8) starts the image adjustment process.

In Step S110, the marker image processing unit 42B (see FIG. 8) extracts a marker pattern from the marker-given image group and generates marker-extracted images 73-1 and 73-2.

In Step S111, the marker image processing unit 42B (see FIG. 8) performs rotation, magnification, and the connection of the vertical position on the basis of the marker patterns of the marker-extracted images 73-1 and 73-2 to calculate a correction parameter.

In Step S112, the marker image processing unit 42B (see FIG. 8) connects the horizontal positions on the basis of the marker patterns of the marker-extracted images 73-1 and 73-2 to calculate a correction parameter and ends the process shown in FIGS. 21A to 21E.

FIG. 21B is a diagram illustrating the imaging regions 6E-21 and 6E-22 and the laser marker 5E-2. The laser marker 5E-2 is radiated to the common imaging region 61E-21. The captured imaging region 6E-22 is slightly smaller than the original imaging region 62 indicated by a dashed line, is inclined to the left side, and deviates in the upward direction.

Figure 21C:
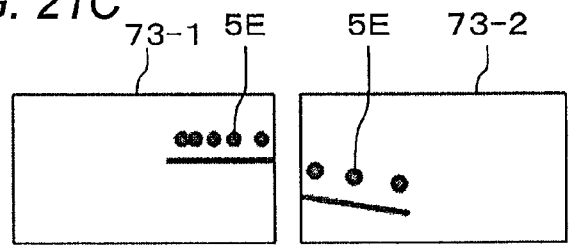

FIG. 21C is a diagram illustrating the marker-extracted images 73-1 and 73-2 generated in Step S110. The laser marker 5E is given to the marker-extracted images 73-1 and 73-2.

Figure 21D:
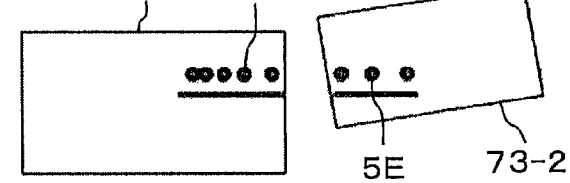

FIG. 21D shows the process in Step S111, in which rotation, magnification, and the connection of the vertical position are performed on the basis of the laser marker 5E which is the marker pattern of the initially captured marker-extracted images 73-1 and 73-2.

Figure 21E:
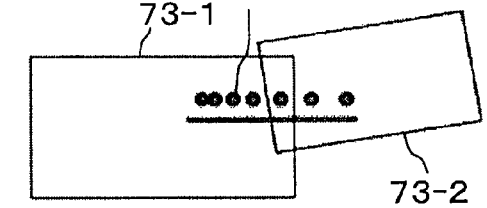

FIG. 21E shows the process in Step S112, in which the horizontal positions of two images which have been connected in Step S111 are further connected to each other on the basis of the laser marker 5E.

In this embodiment, the camera 2E, which is an imaging means, is integrated with the laser device 3E, which is a marker giving means. However, the invention is not limited thereto. The imaging means may not be integrated with the marker giving means.

Effects of Sixth Embodiment

The above-described sixth embodiment has the following effects (J) to (M).

(J) The camera 2E and the laser device 3E are integrally provided. Therefore, it is possible to reduce the number of processes for setting or positioning each camera 2E and each laser device 3E.

(K) The laser marker 5E is formed by one straight line and eight spots. Therefore, it is possible to specify the positional relationship between the patterns of two adjacent images. As a result, it is possible to appropriately adjust the rotation, magnification, vertical position, and horizontal position of two adjacent images.

(L) The eight spots of the laser marker 5E are arranged so as to be equidistant from one horizontal straight line. Therefore, even when any one of the spots is concealed by the unevenness of the object, it is possible to adjust the magnification or horizontal position of two adjacent images on the basis of other spots.

(M) Among the eight spots of the laser marker 5E, the spot on the right side has a large irradiation angle and the spot on the left side has a large irradiation angle. When the distance to the object is short, the right spot with a large irradiation angle is radiated to the common imaging region 61E. When the distance to the object is long, the left spot with a small irradiation angle is radiated to the common imaging region 61E. In this case, the spots are radiated at predetermined intervals on the common imaging region 61E according to the distance to the object. That is, the interval between the spots in the common imaging region 61E has a predetermined value, regardless of the distance to the object and it is possible to appropriately adjust the magnification of the captured image on the basis of the interval between the spots.

Seventh Embodiment

Figure 22:
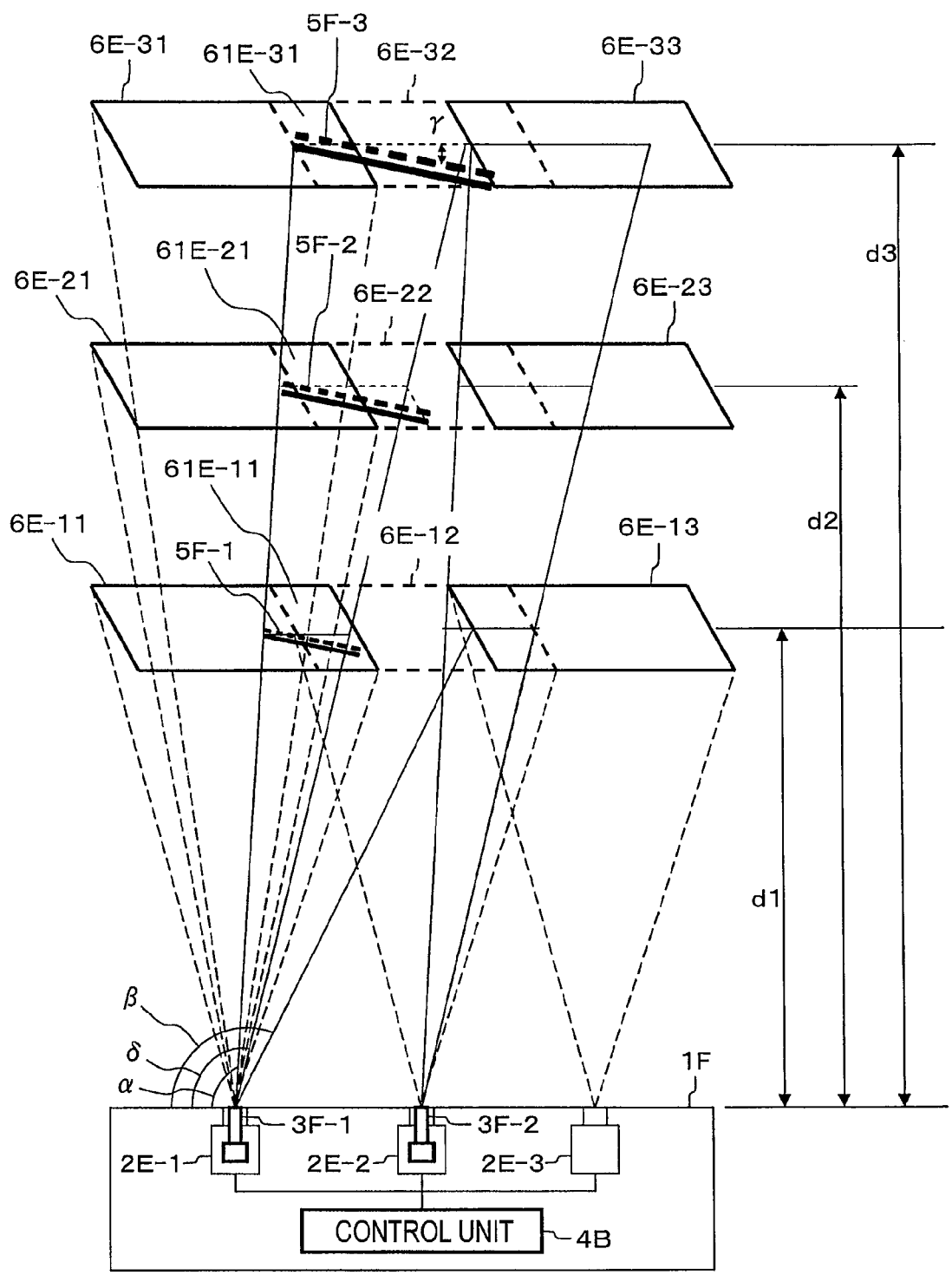
FIG. 22 is a diagram illustrating a plural camera images capturing and processing apparatus according to a seventh embodiment.

FIG. 22 is a diagram illustrating a plural camera images capturing and processing apparatus 1F according to a seventh embodiment. The same components as those in the plural camera images capturing and processing apparatus 1E according to the sixth embodiment shown in FIG. 20 are denoted by the same reference numerals.

The plural camera images capturing and processing apparatus 1F according to the seventh embodiment includes laser devices 3F-1 and 3F-2 which are different from those in the sixth embodiment. Hereinafter, when the laser devices 3F-1 and 3F-2 are not particularly distinguished from each other, they are simply referred to as laser devices 3F.

The laser device 3F-1 radiates a laser marker 5F-1 which is inclined at an angle γ with respect to the laser marker 5E according to the sixth embodiment to a common imaging region 61E-11 which is an overlap region between adjacent imaging regions 6E-11 and 6E-12. The laser device 3F-1 radiates a laser marker 5F-2 to a common imaging region 61E-21 which is an overlap region between adjacent imaging regions 6E-21 and 6E-22. The laser device 3F-1 radiates a laser marker 5F-3 to a common imaging region 61E-31 which is an overlap region between adjacent imaging regions 6E-31 and 6E-32.

The laser device 3F-1 radiates laser beams in the range of an irradiation angle α to an irradiation angle δ.

The right end of the laser marker 5F-1 is set so as to be aligned with the right end of the imaging region 6E-11. In this case, the laser device 3F-1 radiates laser beams at the irradiation angle δ.

The left end of the laser marker 5F-1 is set so as to be aligned with the left end of the common imaging region 61E-31. In this case, the laser device 3F-1 radiates laser beams at the irradiation angle α.

Figure 23:
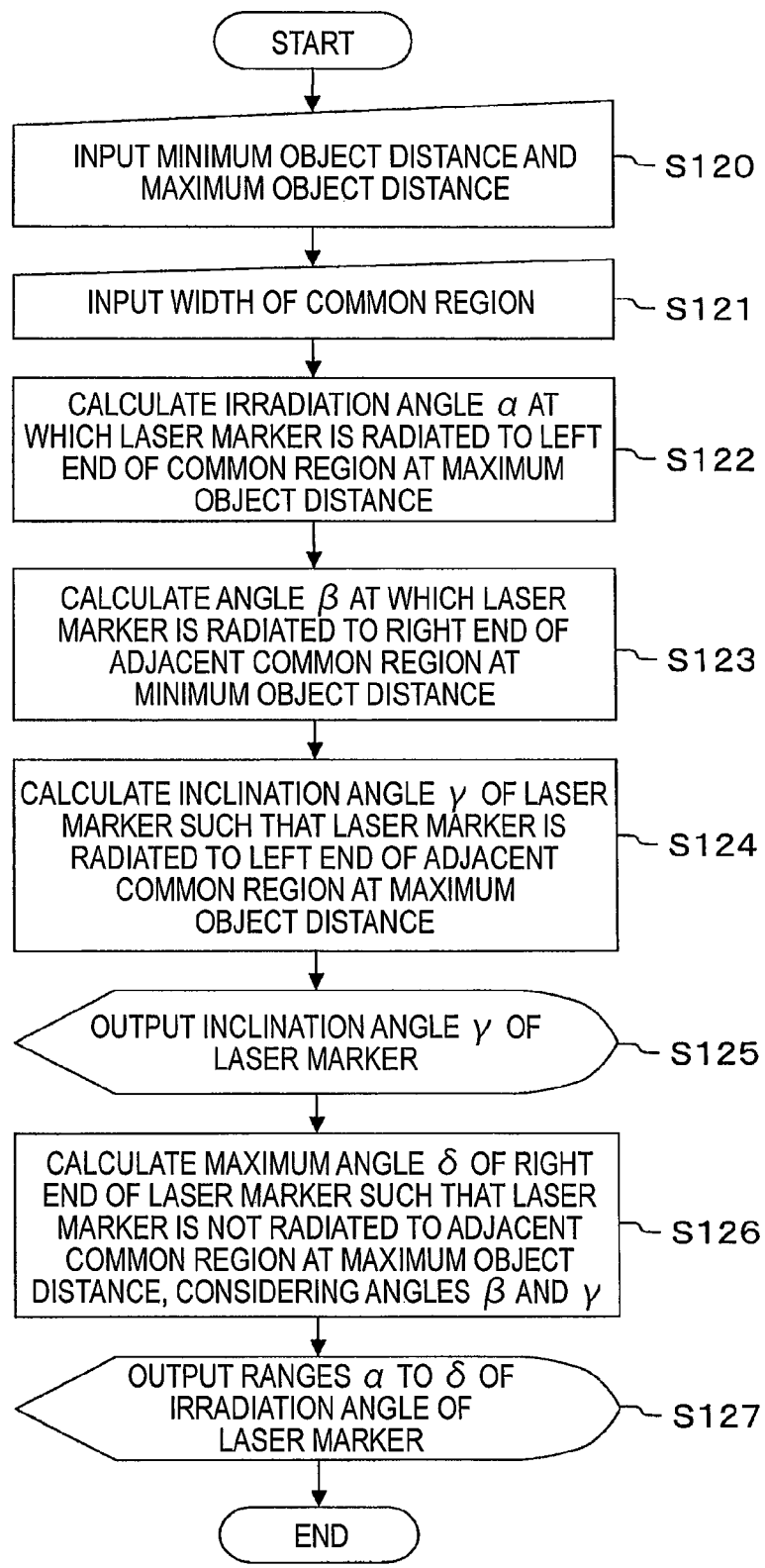
FIG. 23 is a flowchart illustrating a marker pattern setting process according to the seventh embodiment.

FIG. 23 is a flowchart illustrating a marker pattern setting process according to the seventh embodiment.

For example, a software program for the marker pattern setting process is executed on a program to start the marker pattern setting process.

In Step S120, the user of the plural camera images capturing and processing apparatus 1F inputs a minimum object distance d1 and a maximum object distance d3.

In Step S121, the user of the plural camera images capturing and processing apparatus 1F inputs the widths of the common regions. Here, the widths of the common regions mean the widths of the common imaging regions 61E-11 to 61E-31.

In Step S122, the computer calculates the irradiation angle α of the laser beam to the left end of the common region at the maximum object distance d3.

In Step S123, the computer calculates the irradiation angle β of the laser beam to the right end of the common region at the minimum object distance d1.

In Step S124, the computer calculates the inclination angle γ of the laser marker 5F such that the laser beam is not radiated to the left end of an adjacent common region at the maximum object distance d3.

In Step S125, the computer outputs the inclination angle γ of the laser marker 5F.

In Step S126, the computer calculates the maximum irradiation angle δ of the right end of the laser marker 5F at which the laser marker 5F is not radiated to an adjacent common region at the maximum object distance d3, considering the irradiation angle β and the inclination angle γ.

In Step S127, the computer outputs the irradiation angle α and the irradiation angle δ of the laser marker 5F and ends the marker pattern setting process shown in FIG. 23.

The attachment position or attachment angle of each laser device 3F is adjusted on the basis of the inclination angle γ, the irradiation angle α, and the irradiation angle δ to radiate the most appropriate laser marker 5F.

Effects of Seventh Embodiment

The above-described seventh embodiment has the following effects (N) and (O).

(N) The laser marker 5F is an inclined marker pattern. Therefore, it is possible to increase the interval between two spots, as compared to the horizontal marker pattern. As a result, it is possible to accurately adjust the magnification of an image.

(O) The laser marker 5F is inclined with respect to the imaging region 6E. Therefore, even when the irradiation angle α and the irradiation angle δ are set to large values by mistake, the laser beam is not radiated to an adjacent common imaging region 61E and it is possible to prevent the right end of the laser marker 5F from being detected due to errors.

Modifications

The invention is not limited to the above-described embodiments and includes various modifications. For example, the embodiments have been described in detail for ease of understanding of the invention and do not necessarily include all of the above-mentioned structures. Some of the structures according to a given embodiment can be replaced with the structures of other embodiments and the structures of other embodiments can be added to the structures of a given embodiment. In addition, other structures can be added to or replaced with some of the structures of each embodiment or some of the structures of each embodiment can be removed.

For example, some or all of the above-mentioned structures, functions, processing units, and processing means may be implemented by hardware such as an integrated circuit. For example, a processor may interpret and execute a program for implementing each function to implement the above-mentioned structures and functions. Information about programs, tables, and files for implementing each function can be stored in recording devices, such as a memory, a hard disk, and a solid-state drive (SSD), or recording media, such as a flash memory card and a digital versatile disk (DVD).

In each embodiment, control lines or information lines indicate the components which are required in description, but do not indicate all control lines or information lines which are required in products. In practice, it may be considered that almost all structures are connected to each other.

For example, there are the following modifications (a) to (i) of the invention.

(a) The plural camera images capturing and processing apparatuses according to the first to fourth embodiments include two marker giving means and three imaging means and compose three captured images. However, the invention is not limited thereto. The plural camera images capturing and processing apparatus may include one or a plurality of marker giving means and a plurality of imaging means and compose a plurality of captured images.

(b) The plural camera images capturing and processing apparatuses according to the first and second embodiments include the non-visible light (infrared or ultraviolet) marker giving means and the imaging means corresponding to both non-visible light and visible light and generate a visible-light composite image. However, the invention is not limited thereto. The plural camera images capturing and processing apparatus may include a visible light (light with the second wavelength) marker giving means and an imaging means corresponding to both non-visible light (light with the first wavelength) and visible light (light with the second wavelength) and may generate a composite image using non-visible light (light with the first wavelength).

(c) The plural camera images capturing and processing apparatuses according to the first and second embodiments include the non-visible light (infrared or ultraviolet with the second wavelength) marker giving means and the imaging means corresponding to both non-visible light (light with the second wavelength) and visible light (light with the first wavelength) and generate a composite image using visible light (light with the first wavelength). However, the invention is not limited thereto. The plural camera images capturing and processing apparatus may include a marker giving means which uses visible light with a specific wavelength (light with the second wavelength) and an imaging means corresponding to both the visible light (light with the second wavelength) with the specific wavelength and visible light (light with the first wavelength) with a wavelength other than the specific wavelength and may generate a composite image using the visible light (light with the first wavelength) with a wavelength other than the specific wavelength. In addition, the plural camera images capturing and processing apparatus may include a marker giving means which uses non-visible light with a specific wavelength (light with the second wavelength) and an imaging means corresponding to both the non-visible light with the specific wavelength (light with the second wavelength) and non-visible light (light with the first wavelength) with a wavelength other than the specific wavelength and may generate a composite image using the non-visible light (light with the first wavelength) with a wavelength other than the specific wavelength.

(d) In the plural camera images capturing and processing apparatuses 1B according to the third and fourth embodiments, the marker giving means is the visible-light laser device 3B and the imaging device is the visible-light camera 2. However, the invention is not limited thereto. The plural camera images capturing and processing apparatus may be any one of a combination of an infrared laser device and an infrared imaging device, a combination of an ultraviolet laser device and an ultraviolet laser device, a combination of the imaging device and the adhesive droplet marker according to the fifth embodiment, a combination of a far-infrared laser device and a near-infrared imaging device, a combination of a far-infrared laser device and a far-infrared imaging device, a combination of a far-ultraviolet laser device and a near-ultraviolet imaging device, and a combination of a near-ultraviolet laser device and a far-ultraviolet imaging device.

(e) The plural camera images capturing and processing apparatus 1B according to the third embodiment and the plural camera images capturing and processing apparatus 1D according to the fifth embodiment periodically repeat the imaging operation and the moving operation. However, the invention is not limited thereto. The plural camera images capturing and processing apparatus 1B may be constantly moved at a very low speed for a long period of time, capture markerless images and marker-given images in a short time, and generate a composite image, considering these images as still images. In this case, it is possible to constantly move the plural camera images capturing and processing apparatus.

(f) In the third and fourth embodiments, the marker giving means is turned on and off to perform the imaging process. However, the invention is not limited thereto. The markers may be formed at different positions in each imaging region 6 and the images except the positions of the markers may be composed to generate a markerless composite image.

(g) In the plural camera images capturing and processing apparatus 1E according to the sixth embodiment, the odd-numbered cameras 2E or the even-numbered cameras 2E from the right side may be integrated with laser devices 3E which radiate light with different colors (red/blue/green), laser devices 3E which radiate different kinds of light (for example, visible light/infrared/ultraviolet), laser devices 3E which radiate markers with different pattern shapes, or laser devices 3E which radiate markers with different arrangement patterns. In this case, laser markers 5E with different colors, different kinds of light, different pattern shapes, or different arrangement patterns are radiated to adjacent common imaging regions 61E. Therefore, it is possible to prevent an error in the detection of the markers, without the interference of adjacent laser markers 5E with adjacent common imaging regions 61E.

(h) In the plural camera images capturing and processing apparatus 1E according to the sixth embodiment, the odd-numbered laser devices 3E from the right side may be operated to capture the marker-given images and then the even-numbered laser devices 3E from the right side may be operated to alternately capture the marker-given images. In this case, since the laser markers 5E are radiated to adjacent common imaging regions 61E at different times, it is possible to prevent an error in the detection of the marker due to the interference of adjacent laser markers 5E with adjacent common imaging regions 61E. Therefore, it is possible to identify the laser marker 5E in each common imaging region.

(i) In the plural camera images capturing and processing apparatus 1E according to the sixth embodiment, the laser marker 5E is formed by one straight line and eight spots. However, the invention is not limited thereto. The identifiable markers shown in Table 1 may be radiated in a wide range, the marker which satisfies the marker pattern conditions in the common imaging region 61E shown in Table 2 among the identifiable markers may be extracted, and the image adjustment process may be performed. In this case, it is possible to obtain correction parameters for rotation, magnification, and positioning.

What is claimed is:

1. A plural camera images capturing and processing apparatus comprising:
    a plurality of imaging means that capture images of a plurality of adjacent imaging regions which overlap each other;
    one or a plurality of marker giving means that give a marker to each common imaging region in which the imaging regions overlap each other;
    an imaging control means that controls the imaging means and the marker giving means and acquires a markerless image group in which no marker is given to the common imaging region and a marker-given image group in which the marker is given to the common imaging region;
    a correction parameter calculation means that calculates a correction parameter for connecting the imaging regions using the marker-given image group; and
    an image composition means that composes the markerless image group to generate a composite image on the basis of the correction parameter.

2. The plural camera images capturing and processing apparatus according to claim 1,
    wherein the imaging means can capture light with a first wavelength and light with a second wavelength, and
    the marker giving means gives a marker of the light with the second wavelength to the common imaging region.

3. The plural camera images capturing and processing apparatus according to claim 2,
    wherein a combination of the light with the first wavelength and the light with the second wavelength is any one of a combination of visible light and non-visible light, a combination of non-visible light and visible light, a combination of visible light with a specific wavelength and visible light with a wavelength other than the specific wavelength, and a combination of non-visible light with a specific wavelength and non-visible light with a wavelength other than the specific wavelength.

4. The plural camera images capturing and processing apparatus according to claim 1,
    wherein the imaging means can capture at least one of visible light and non-visible light, and
    the imaging control means acquires the marker-given image group and the markerless image group at different times.

5. The plural camera images capturing and processing apparatus according to claim 4,
    wherein the imaging control means sequentially acquires a first markerless image group, the marker-given image group, and a second markerless image group, and
    the image composition means interpolates or extrapolates the first markerless image group and the second markerless image group to generate the composite image to which no marker is given at the time when the marker-given image group is captured.

6. The plural camera images capturing and processing apparatus according to claim 4,
    wherein the imaging control means sequentially acquires a first marker-given image group, the markerless image group, and a second marker-given image group, and
    the correction parameter calculation means calculates the correction parameter, which is information for aligning the inclinations, sizes, and positions of the imaging regions, using the first marker-given image group and the second marker-given image group.

7. The plural camera images capturing and processing apparatus according to claim 1,
    wherein, when a first image group in which no marker is given to a front part of the imaging region in a moving direction is acquired, the imaging control means instructs the marker giving means to give an marker, which is at least stable until acquiring an image after the apparatus moving, to the front part of the imaging region in the moving direction and acquires a second image group,
    when the imaging region is moved such that the marker is disposed in a rear part in the moving direction, the imaging control means acquires the next first image group,
    the correction parameter calculation means calculates the correction parameter, which is information for aligning the inclinations, sizes, and positions of the imaging regions, on the basis of the second image group and the next first image group, and
    the image composition means composes the first parts of the imaging regions in the moving direction in the first image group to generate the composite image on the basis of the correction parameter.

8. The plural camera images capturing and processing apparatus according to claim 7,
    Wherein, the marker, which is at least stable until acquiring an image after the apparatus moving, is an adhesive marker.

9. The plural camera images capturing and processing apparatus according to claim 1,
    wherein the marker giving means gives at least two markers to each common imaging region and gives at least one marker to the imaging regions other than the common imaging region.

10. The plural camera images capturing and processing apparatus according to claim 1,
    wherein each imaging means is integrated with each marker giving means, and
    the marker giving means gives a predetermined pattern of marker to the common imaging region.

11. The plural camera images capturing and processing apparatus according to claim 1,
    wherein the marker giving means gives, to the common imaging regions, markers with different pattern shapes including points, lines, circles, or polygons with different sizes or directions, markers with different arrangements, directions, intervals, or sizes for limiting the number of patterns in a row of at least two pattern shapes in the direction of the captured image, markers with different arrangements, directions, intervals, or sizes for limiting the number of patterns in a row of at least three pattern shapes, markers with different colors, markers with different kinds of light, or any one of combinations of the markers as a predetermined pattern of marker.

12. The plural camera images capturing and processing apparatus according to claim 11,
   wherein three or more imaging means are provided, and
   the marker giving means gives the predetermined pattern of marker to the common imaging region in a distance range of a minimum distance to a maximum distance to an object and does not give the predetermined pattern of marker to adjacent common imaging regions of adjacent common imaging regions at the maximum distance to the object such that the predetermined pattern of marker is not given to adjacent common imaging regions.

13. The plural camera images capturing and processing apparatus according to claim 11,
   wherein three or more imaging means are provided, and
   each marker giving means gives any one of markers with different colors, markers with different shapes, markers with different arrangements, and markers with different giving times to adjacent common imaging regions.

14. A composite imaging method comprising:
   capturing images of a plurality of adjacent imaging regions which overlap each other using a plurality of imaging means and acquiring a markerless image group to which no marker is given;
   giving a marker to each common imaging region in which the imaging regions overlap each other using one or a plurality of marker giving means;
   capturing the image of each imaging region using the plurality of imaging means;
   acquiring a marker-given image group to which the marker is given from the plurality of imaging means;
   calculating a correction parameter for connecting the imaging regions on the basis of the marker-given image group, using a correction parameter calculation means; and
   composing the markerless image group to generate a composite image on the basis of the correction parameter, using an image composition means.

* * * * *